(12) United States Patent  
Vaidya

(10) Patent No.: US 8,814,866 B2  
(45) Date of Patent: Aug. 26, 2014

(54) METHOD FOR MINIMALLY INVASIVE TREATMENT OF UNSTABLE PELVIC RING INJURIES

(76) Inventor: Rahul Vaidya, Tecumseh (CA)

( * ) Notice: Subject to any disclaimer, the term of this patent is extended or adjusted under 35 U.S.C. 154(b) by 266 days.

(21) Appl. No.: 13/494,684

(22) Filed: Jun. 12, 2012

(65) Prior Publication Data

US 2012/0259370 A1 Oct. 11, 2012

Related U.S. Application Data

(63) Continuation-in-part of application No. 13/470,608, filed on May 14, 2012, which is a continuation of application No. 12/287,280, filed on Oct. 9, 2008, now Pat. No. 8,177,785, application No. 13/494,684, which is a continuation-in-part of application No. 12/590,988, filed on Nov. 18, 2009, now Pat. No. 8,398,635.

(51) Int. Cl.
| | | |
|---|---|---|
| A61B 17/56 | (2006.01) | |
| A61B 17/58 | (2006.01) | |
| A61F 2/30 | (2006.01) | |
| A61B 17/64 | (2006.01) | |

(52) U.S. Cl.  
CPC .................................. *A61B 17/6433* (2013.01)

USPC ........................ 606/60; 606/286; 606/86 R

(58) Field of Classification Search  
USPC ..................... 606/54, 57, 59, 246, 264, 265, 606/267–271, 279  
See application file for complete search history.

(56) References Cited

U.S. PATENT DOCUMENTS

| 5,527,310 A | 6/1996 | Cole et al. |
| 2005/0277928 A1 | 12/2005 | Boschert |
| 2008/0108989 A1 | 5/2008 | Parsell et al. |
| 2010/0042149 A1 | 2/2010 | Chao et al. |

OTHER PUBLICATIONS

Sciulli, Robert. "CT-Guided Iliosacral Screw Placement: Technique and Clinical Experience." American Journal of Roentgenology 188 (2007): W181-W192.

*Primary Examiner* — Andrew Yang  
*Assistant Examiner* — Olivia C Chang  
(74) *Attorney, Agent, or Firm* — David W. Schumaker

(57) ABSTRACT

The instant invention is a novel method for construct for temporary or definitive pelvic stabilization. The method uses the already established principles of anterior external fixation combined with internal hardware placed in a minimally invasive fashion. Fixation means are affixed to the ilia and both a rigid, subcutaneous anteriorly bowed elongated plate and a subcutaneous posterior plate are connected between the fixation means.

15 Claims, 18 Drawing Sheets

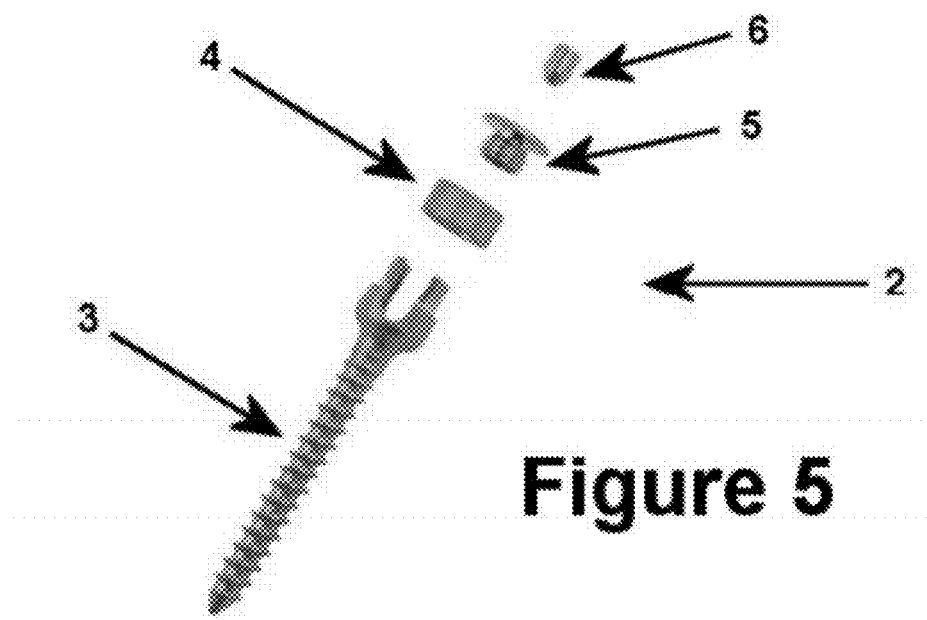
Figure 5
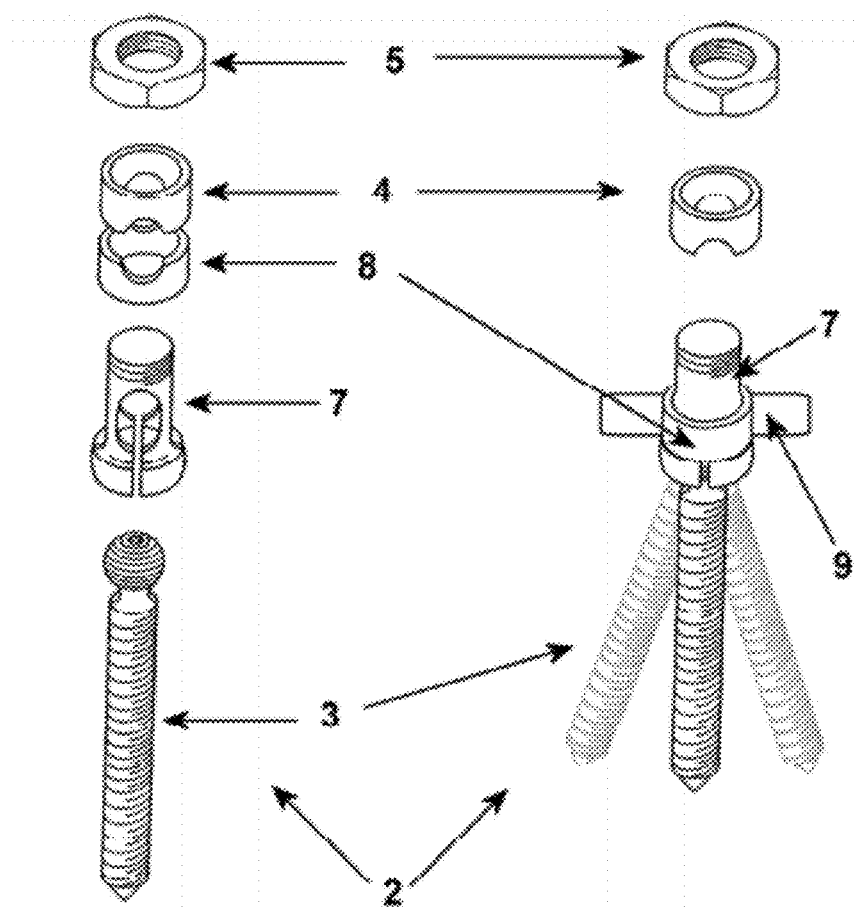
Figure 6a  Figure 6b

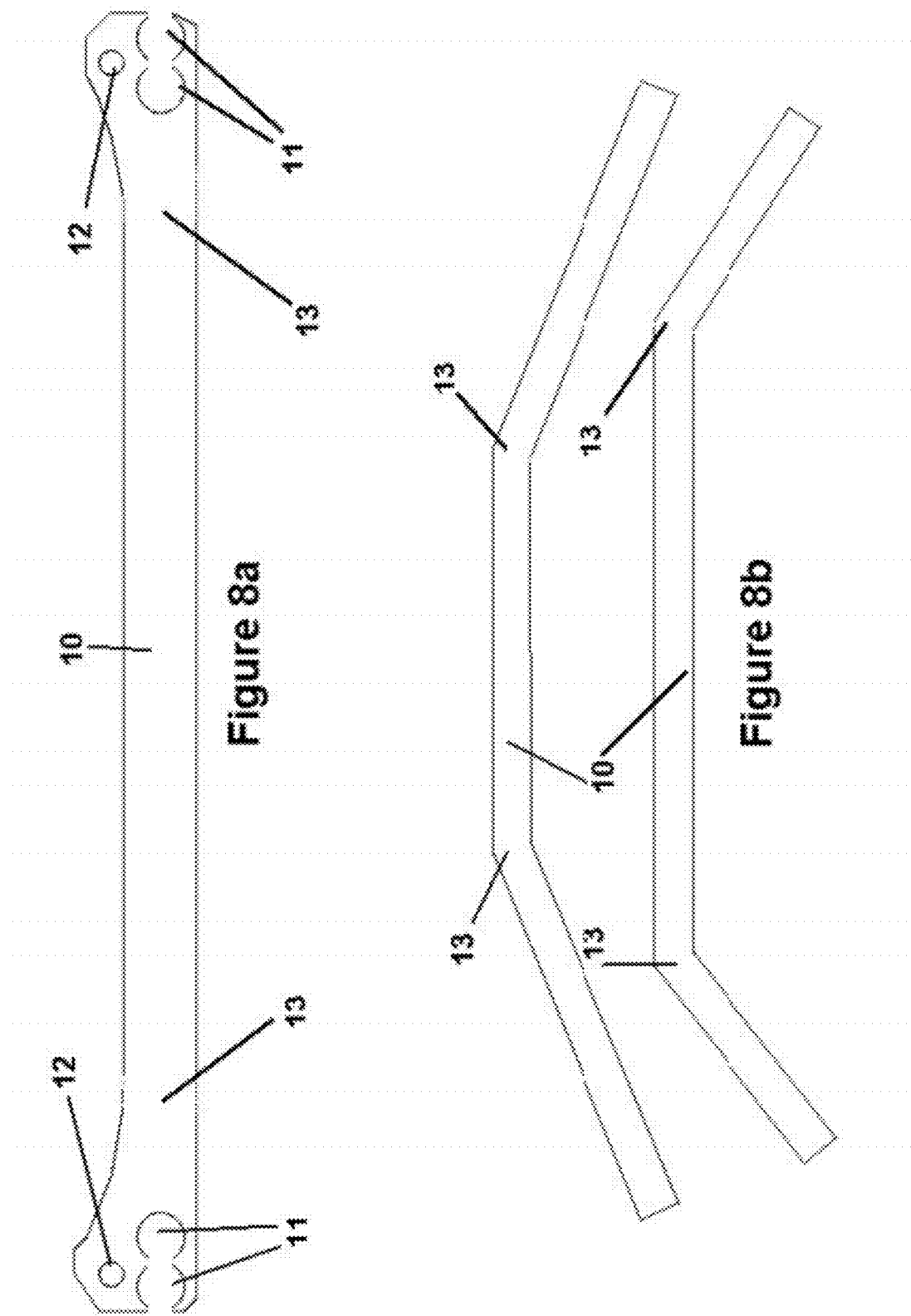

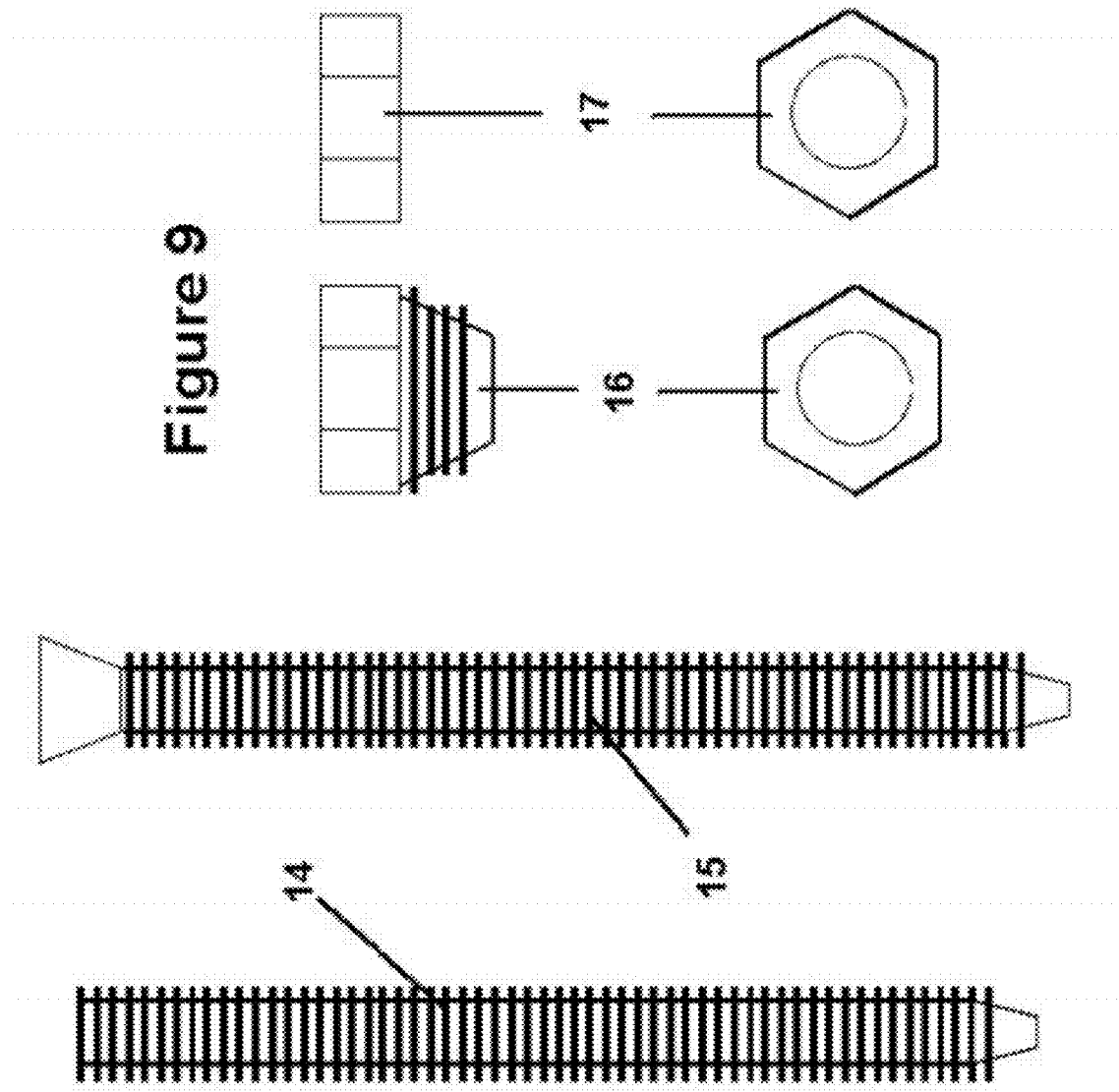

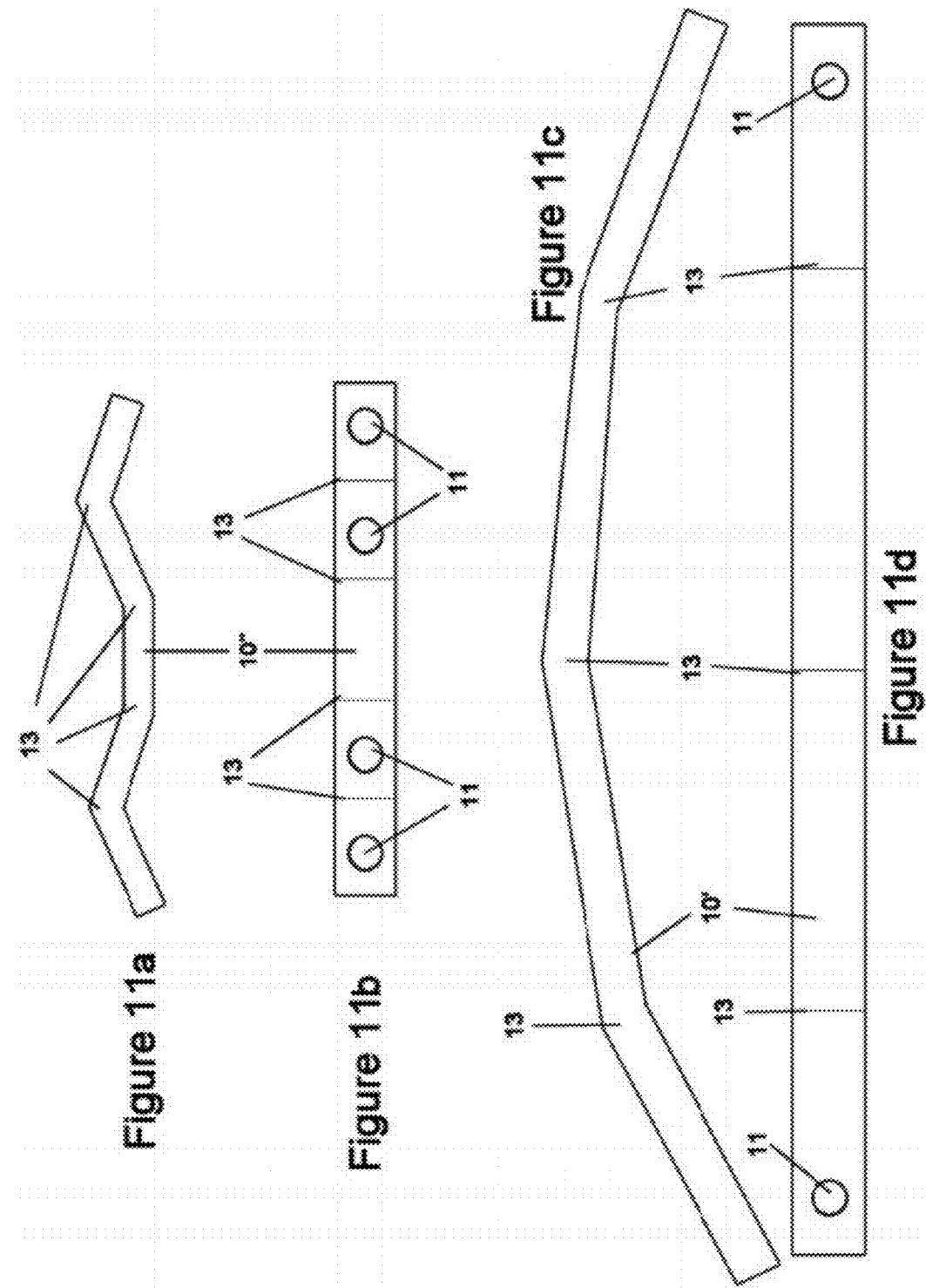

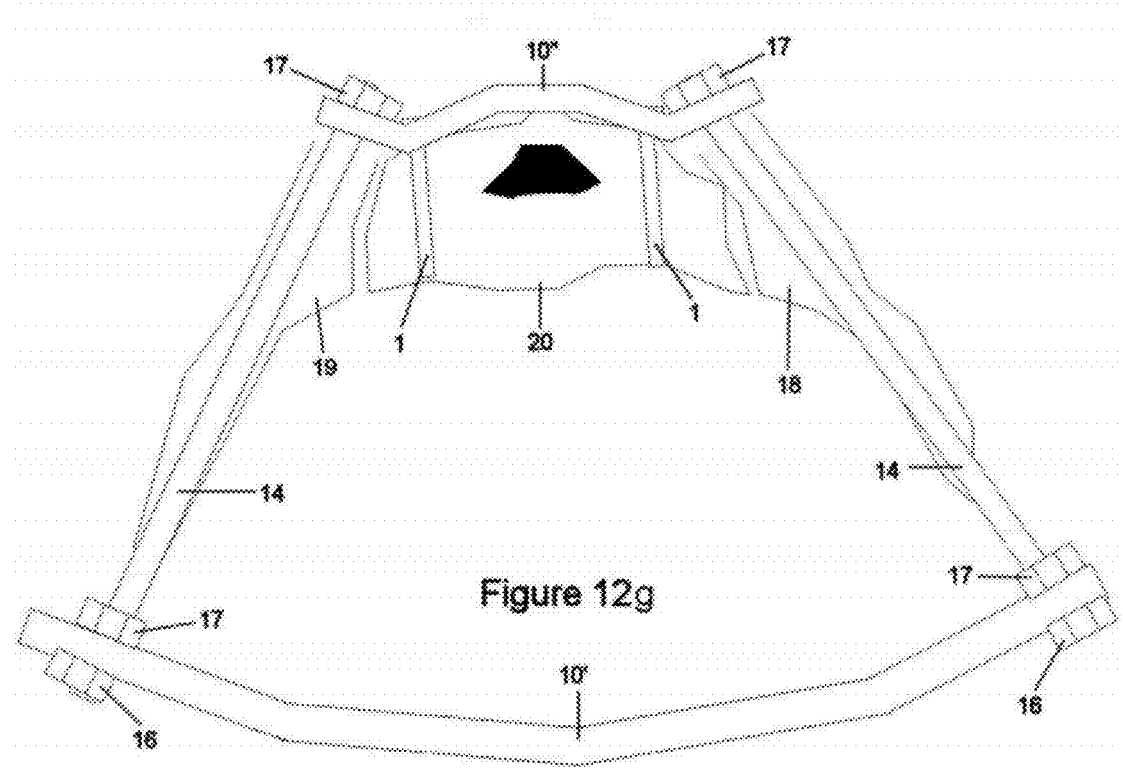

METHOD FOR MINIMALLY INVASIVE TREATMENT OF UNSTABLE PELVIC RING INJURIES

RELATED APPLICATIONS

This application is a continuation-in-part of U.S. application Ser. No. 13/470,608 filed May 14, 2012 and entitled "Method for Minimally Invasive Treatment of Unstable Pelvic Ring Injuries with an Internal Anterior Fixator and Posterior Iliosacral Screws", which is a continuation of U.S. application Ser. No. 12/287,280 filed Oct. 9, 2008, now U.S. Pat. No. 8,177,785. This application is also a continuation-in-part of U.S. application Ser. No. 12/590,988 filed Nov. 18, 2009 and entitled "Method for Minimally Invasive Treatment of Unstable Pelvic Ring Injuries" (now published as U.S. Patent Application Publication number 2010-0198267).

FIELD OF THE INVENTION

The instant invention relates generally to methods and apparatus for the treatment of unstable pelvic fractures. More specifically the invention relates to a method and apparatus for minimally invasive treatment of unstable pelvic ring injuries using both anterior and posterior internal fixators.

BACKGROUND OF THE INVENTION

Unstable pelvic fractures typically occur as a result of high-energy injuries such as automobile accidents, falls and the like. Even in this age of modern polytrauma care, acute pelvic fractures are potentially lethal. In the past, such injuries were treated without surgery. However, recovery to completely normal functionality was the exception rather than the norm. In more modern times, unstable pelvic fractures are treated surgically with a number of techniques depending on the type and extent of the fracture(s).

The pelvis consists of three major bones (two ilium and the sacrum) and some minor bones joined together in a ring shape and held by strong ligaments, See FIG. 1. General characteristics of pelvic fracture include severe pain, pelvic bone instability, and associated internal bleeding. Devices and methods used to treat fracture of the pelvis currently fall under two general classifications; internal fixation and external fixation. Combinations of both techniques are frequently chosen for certain fracture patterns.

Internal fixation is typically utilized when the patient exhibits unstable posterior pelvic fractures. Internal fixation refers to plates and screws applied directly onto the fracture sites after realignment. See, for example, U.S. Pat. Nos. 4,454,876; 5,108,397; 6,340,362 and 6,440,131. This type of fracture tends to be more complex with it involving multiple bony structures. Internal fixation addresses these clinical issues through open reduction and correction of misaligned bone segments that are subsequently stabilized with a wide variety of plate and screw methods.

Anterior pelvic fractures or hemodynamically unstable patients are candidates for external fixation. Pelvic external fixation consists of pins usually inserted into the iliac bones and then connected together by clamps and bars. See, for example, U.S. Pat. Nos. 4,292,964; 4,361,144; 5,350,378 and 6,162,222. External fixation methods consists of stabilizing the pelvic ring with a rigid framework residing outside the patient's body that is connected to the patient's pelvis via multiple pins that penetrate through the patient's soft and hard tissues. Several frame types are currently utilized. Two of the more widely deployed devices for external pelvic stabilization are the Hoffmann 2 Inverted "A" Frame and the Ganz Pelvic C Clamp.

The application of external reduction and fixation for pelvic fractures is advantageous compared to internal reduction and fixation due to its speed of deployment and lower level of technical training required for utilization. The primary disadvantages of external fixation of pelvic fractures include high risk of pin tract infections, and general patient discomfort. Also, the external frame physically blocks subsequent surgery on the abdomen and they are frequently difficult to fit to obese patients.

The instant inventor has developed a novel method using the already established principles of anterior external fixation. By combining these principles with internal hardware placed in a minimally invasive fashion, this technique allows for definitive pelvic stabilization without having the issues and co-morbidities of an external fixator (i.e. interfering with other procedures, pin care, patient acceptance, later conversion to internal fixation, etc.)

SUMMARY OF THE INVENTION

A surgical method for minimally invasive treatment of unstable pelvic ring injuries which comprises the steps of: affixing at least one fixation means to each of the first and second ilium of the pelvis; the fixation means comprising a threaded rod which is inserted into the ilium at the ASIS and extends through the ilium to the PSIS, attaching a rigid, anteriorly bowed subcutaneous elongated anterior plate to at least one of the fixation means on each of the first and second ilium, anterior to the pelvis; and attaching a subcutaneous posterior plate to at least one of the fixation means on each of the first and second ilium, posterior to the pelvis.

The surgical method may further comprise the steps of: creating a longitudinal incision centered on the Anterior Superior Iliac Spine (ASIS); bluntly dissecting through the soft tissues; using fluoroscopic imaging to identify the starting point for the threaded rod; opening the cortex of the ilium at the starting point with a drill; establishing a corridor between the inner and outer cortices of the ilium using a pedicle finder; and screwing the threaded rod into the corridor.

The surgical method wherein the step of screwing the threaded rod into the corridor may comprise screwing the threaded rods such that the threaded rods extend through the ilium to the PSIS. The surgical method may further comprise subcutaneously tunneling the elongated anterior plate from one of the fixation means on one ilium to another of the fixation means on the other ilium, anterior to the pelvis, before the step of attaching the elongated anterior plate. The elongated anterior plate may have at least one hole in each end to accommodate the threaded rod fixation means which affix the plate to the anterior of each of the first and second ilium of the pelvis.

The surgical method may further include the steps of: threading a first threaded nut onto each of the threaded rods affixed to each of the first and second ilium of the pelvis; inserting one of the threaded rods affixed to the ilia into the holes in the either end of the elongated plate, the elongated plate resting on the first threaded nuts; threading a second threaded nut onto each of the threaded rods affixed to the ilia; and tightening the second threaded nuts against the elongated anterior plate such that the first threaded nuts and the second threaded nuts hold the elongated anterior plate securely to the threaded rod affixed to the ilia. The elongated anterior plate may have bends to give the plate an approximation of an arc shape. The elongated anterior plate may be positioned with the arc anterior to avoid any potential compressive complications to genitourinary or neurovascular structures prior to the step of attaching.

The subcutaneous posterior plate may have a first hole in each end to accommodate the threaded rod fixation means which affix the subcutaneous posterior plate to the posterior of each of ilium of the pelvis. The surgical method may further comprise the step of removing the ilium bone adjacent to the posterior end of the threaded rods, prior to attaching the subcutaneous posterior plate. The surgical method may further comprise the step of subcutaneously tunneling the subcutaneous posterior plate from one of the fixation means on one ilium to another of the fixation means on the other ilium, posterior to the pelvis, before the step of attaching the subcutaneous posterior plate. The surgical method may further comprise the step of inserting the posterior ends of the threaded rods into the holes in the either end of the subcutaneous posterior plate, the subcutaneous posterior plate resting on the ilia and the sacrum.

The surgical method may further comprise the steps of threading a threaded nut onto each of the posterior end of the threaded rods affixed to the ilia; and tightening the threaded nuts against the subcutaneous posterior plate such that the threaded nuts hold the subcutaneous posterior plate securely to the threaded rod pressed against the ilia and the sacrum. The subcutaneous posterior plate may have a second hole in each end, interiorly position from the first hole to accommodate sacral fixation screws, and the method may further comprise the step of inserting sacral fixation bone screws through each of the second holes and into the sacrum. The surgical method may further include the step of leaving the fixation means and the plates attached to the pelvis for 8 to 12 weeks and thereafter removing the fixation means and the plates.

BRIEF DESCRIPTION OF THE DRAWINGS

FIG. 5 depicts another embodiment of a pedicle screw system useful in the anterior pelvic stabilization surgical method of the present invention;

FIGS. 6a and 6b depict yet another embodiment of a pedicle screw system useful in the anterior pelvic stabilization surgical method of the present invention;

FIGS. 8a and 8b show different views of an elongated plate which may be used in an alternative embodiment of the present invention and is used in place of the bowed rod;

FIG. 9 depicts threaded rods, screws, caps, and nuts useful in conjunction with the alternative embodiment to affix the elongated plate to the pelvis;

FIGS. 11a-11d show different views of an elongated anterior plate and a subcutaneous posterior plate which may be used in yet another alternative embodiment of the present invention; and FIGS. 12a-12g depict different stages in the surgical technique for fixation of the unstable pelvic ring injury using the elongated anterior plate and subcutaneous posterior plate of FIGS. 11a-11d.

DETAILED DESCRIPTION OF THE INVENTION

The instant invention is a novel method and construct for temporary or definitive pelvic stabilization. The method uses the already established principles of anterior external fixation combined with internal hardware placed in a minimally invasive fashion. Stabilization of pelvic ring injuries is most often indicated when the volume of the pelvis is increased and/or an unstable pattern of injury is present. This stabilization method must be applied in the operating room under sterile conditions with adequate fluoroscopic guidance. It can be utilized in an emergent setting following provisional stabilization in the emergency room with a pelvic binder, sheet or clamp.

To aid in the determination of utilizing this anterior fixation method, we prefer the Tile classification since it is based on the concept of pelvic stability. In the Tile classification, type A fractures involve a stable pelvic ring. The partially stable type B lesions, such as "open-book" and "bucket-handle" fractures, are caused by external and internal rotation forces, respectively. In type C injuries, there is complete disruption of the posterior sacroiliac complex. These unstable fractures are almost always caused by high-energy severe trauma associated with motor vehicle accidents, falls from a height, or crushing injuries. Type A and type B fractures make up 70% to 80% of all pelvic injuries. This fixation method is typically considered for Tile B and C type injuries. In many patients with partially stable injury patterns, the presence of significant pain with upright posture can be alleviated with the addition of anterior fixation. Supra-acetabular fixation has been shown to have biomechanical advantages compared to iliac crest fixation. If adequate reduction cannot be obtained in a closed manner, then more traditional open reduction techniques need to be employed.

Surgical Technique First Embodiment

The patient may be positioned in the supine position on a radiolucent table. The skin may be prepped and draped from above the umbilicus to the proximal thigh. The lower extremity may be prepped into the field as well to facilitate reduction techniques.

Figure 1:
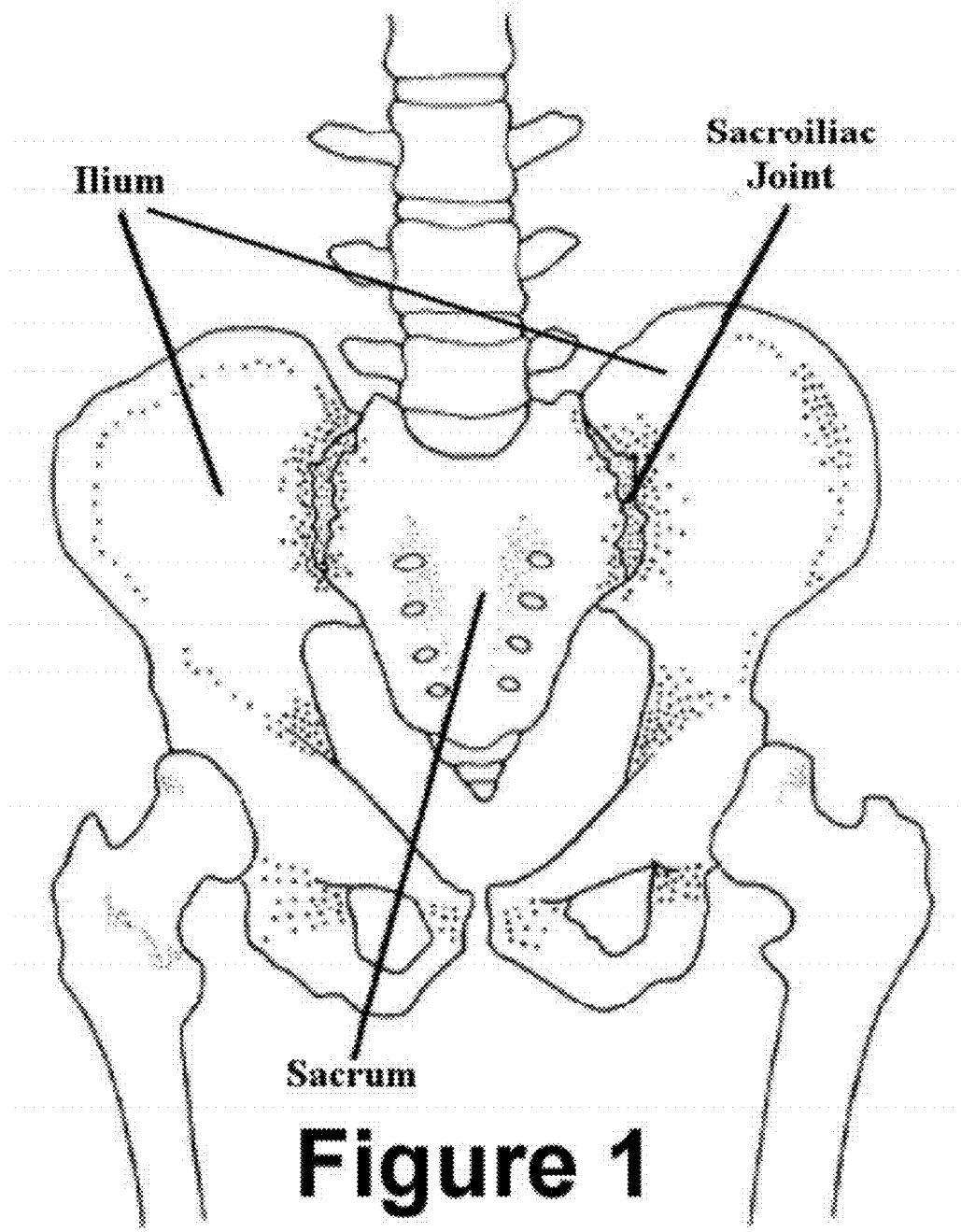
FIG. 1 shows a diagrammatic depiction of a pelvis.
Figure 2:
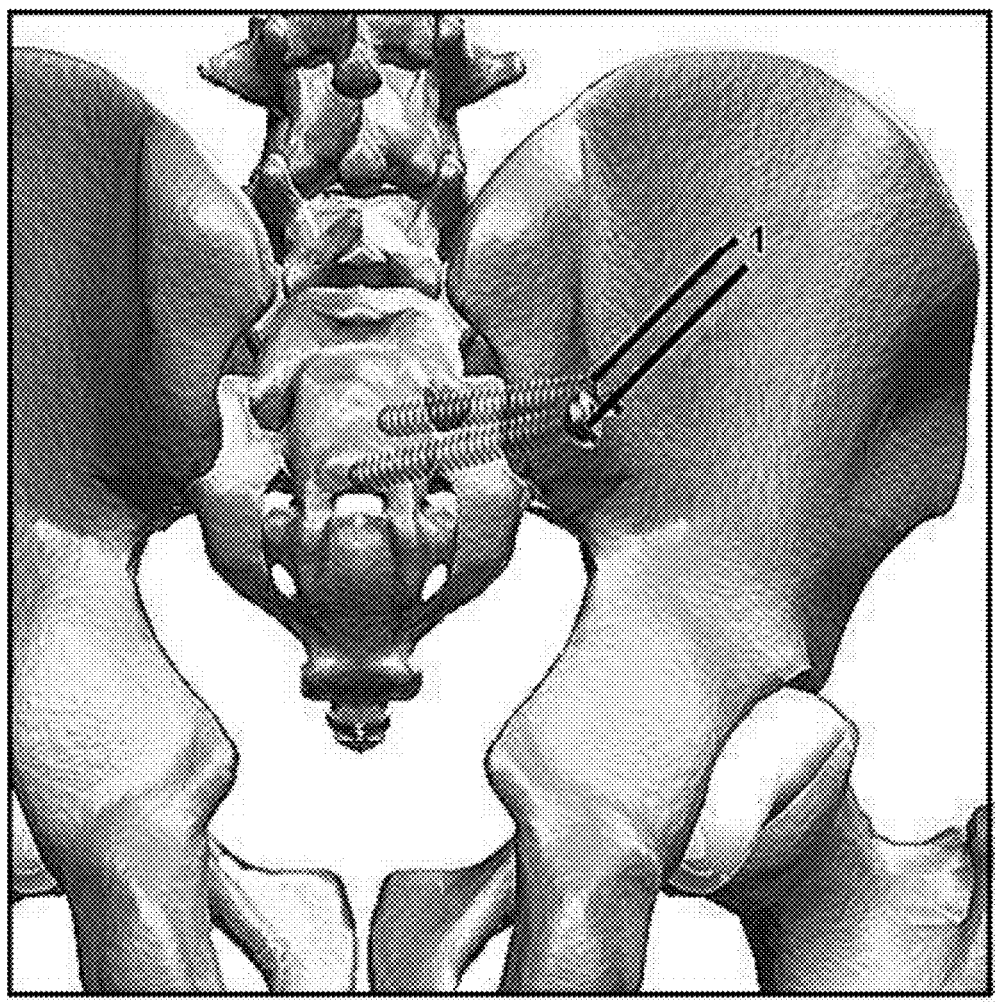
FIG. 2 shows the method in which iliosacral screws are used to perform posterior stabilization of the sacroiliac joint of the pelvis.
Figure 3:
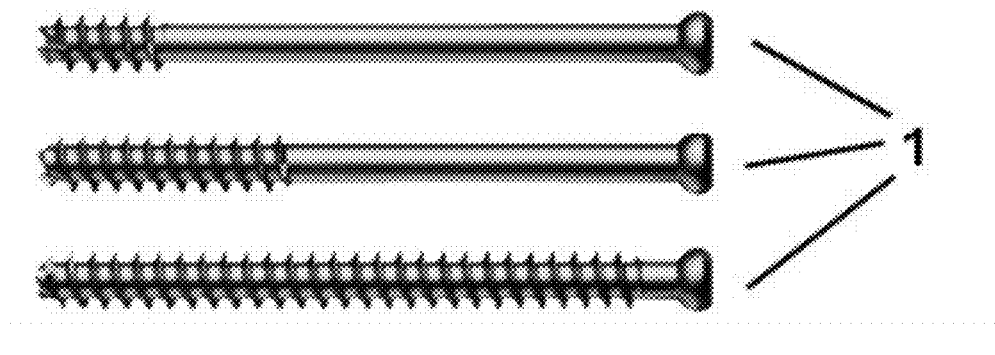
FIG. 3 depicts a variety of iliosacral screws useful for the posterior stabilization of the sacroiliac joint of the pelvis.

The posterior instability may be addressed first. The procedure for placement of iliosacral screws for posterior pelvic instability has been well described and will not be discussed here. See for example "CT-Guided Iliosacral Screw Placement: Technique and Clinical Experience" by Robert L. Sciulli, et al., American Journal of Roentgenology 2007; 188: W181-W192 (reproduced at http://www.ajronline.org/cgi/content/full/188/2/W181). FIG. 2 illustrates the way in which iliosacral screws 1 are inserted through the rear of the ilium and into the sacrum, thus stabilizing the posterior instability. FIG. 3 depicts typical iliosacral screws 1.

After stabilizing the posterior elements via the iliosacral screws, the anterior pelvis may be addressed. A longitudinal incision (preferably 2-3 cm in length) may be made centered between the Anterior Inferior Iliac Spine (AIIS) and the Anterior Superior Iliac Spine (ASIS). Blunt dissection may be used through the soft tissues. Potential dangers in this area include the lateral femoral cutaneous nerve, and care should be taken not to violate the hip capsule. Fluoroscopic imaging may be used to identify the starting point of the supra-acetabular fixation screw. The beam should be directed in an obturator oblique and pelvic outlet direction in order to isolate the appropriate column of bone for screw placement. A recent article by Gardner and Nork describes the appropriate placement of supra-acetabular pins in excellent detail. See "Stabilization of Unstable Pelvic Fractures With Supraacetabular Compression External Fixation", Gardner, et al., Journal of Orthopaedic Trauma 2007; 4:269-273. Once the appropriate starting point is identified, the cortex may be opened with a drill (preferably 5.0 mm). A pedicle finder is then used to establish a corridor between the inner and outer cortices of the ilium. Pedicle screws (preferably USS 8 mm×80 mm) are placed in the supra-acetabular position under fluoroscopic guidance.

Figure 4:
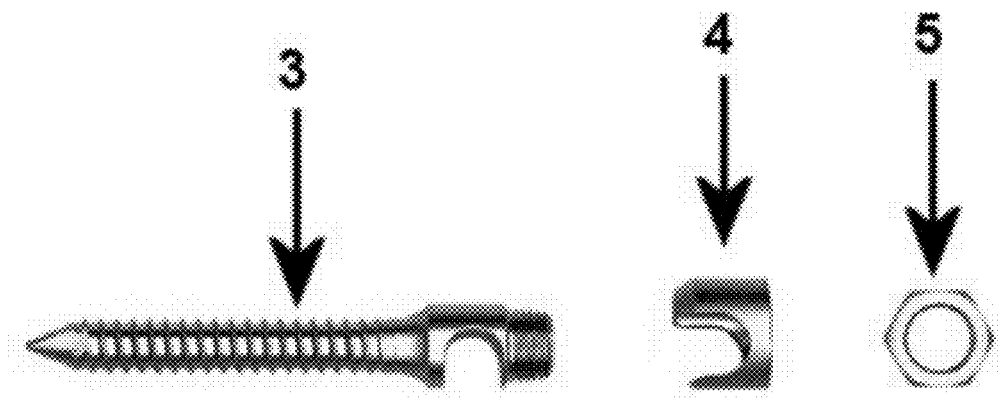
FIG. 4 depicts one embodiment of a pedicle screw system useful in the anterior pelvic stabilization surgical method of the present invention.

FIGS. 4, 5, 6a and 6b show exploded views of three different types of pedicle screw 2 which may be useful in the method of the present invention. Referring to FIG. 4, the separate parts of a side-opening pedicle screw can be seen. Specifically shown are the screw 3, the sleeve 4 and the nut 5. In use, the sleeve 4 and nut 5 are placed over the screw 3 and hold a rod in the cylindrical opening formed by the mating of the screw 3 and the sleeve 4. Turning to FIG. 5, a different type of pedicle screw 2 is seen. In this variety, there is still a screw 3, a sleeve 4 and a nut 5, but there is also a set screw 6 which helps to hold a rod in the opening between the screw 3 and the sleeve 4. Finally, FIGS. 6a and 6b show a polyaxial pedicle screw having a swivel joint. Once again this variety of pedicle screw has a screw 3, a sleeve 4 and a nut 5, but this type also has a mechanism consisting of a swivel clamp 7 and a swivel clamp collar 8. This added hardware allows the head of the pedicle screw to swivel somewhat independently from the screw 3. Thus this swivel head allows for ease of fit to curved rods 9 without the requirement for excessive rod contouring.

Returning to the surgical method, it should be noted that the screws are preferably not seated completely to the bone so that the connecting rod may be passed superficial to the sartorius muscles. A titanium rod 9 (preferably USS 6 mm) may then be pre-contoured with a bow, placed over the screws 2 and cut to the appropriate length on the back table. The rod may preferably be anywhere from 6 mm to 1 cm in diameter and may also be pre-bent for ease of use. The rod may then be tunneled subcutaneously from one screw to the other. Before connecting the rod, it may be positioned with the bow anterior to avoid any potential compressive complications to genitourinary or neurovascular structures. Also, any necessary reduction may be performed at this stage. Rotational and vertical alignment should be performed prior to attaching the rod, and preferably prior to tunneling the rod to limit pressure on the soft tissues. If posterior fixation is used, then most of the reduction should be complete at this point. This hardware system allows for compression and tensioning once the rod is in place. Reduction and hardware position may be assessed on fluoroscopic AP, inlet and outlet views. As an alternative to fluoroscopic AP, CT guidance may be used. The construct is intended as definitive treatment, with removal typically performed after 8 to 12 weeks. The timing of application and removal is ultimately determined on an individual case basis.

Figure 7:
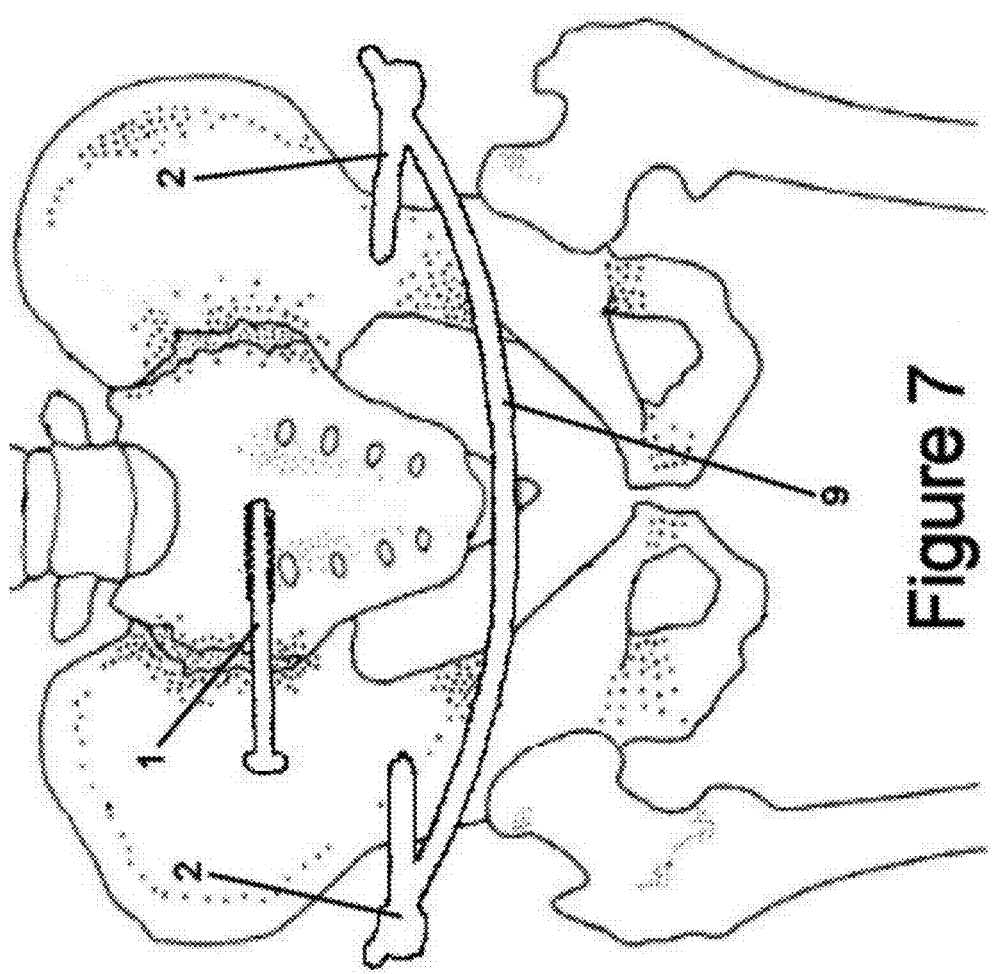
FIG. 7 is an x-ray of a patient who has had posterior stabilization of the sacroiliac joint of the pelvis using an iliosacral screw as well as the anterior stabilization surgical method of the present invention using two pedicle screws and an anteriorly bowed rod.

FIG. 7 shows an x-ray of a 32-year old male who was involved in a motor vehicle accident and upon whom the inventive surgical method was performed. As can be seen, the posterior was stabilized and fixated using an iliosacral screw 1. The anterior was fixated and stabilized by the inventive method using two pedicle screws 2, one attached to the supra-acetabular portion of each ilium. Connected between the pedicle screws 2 is a rigid, anteriorly bowed subcutaneous fixation rod 9.

The biomechanical stability of the inventive supra-acetabular pedicle screw internal fixation construct was evaluated and compared with the more prevalent external fixator. Three different pedicle screw constructs were compared to the external fixator, a mono axial screw system and two different polyaxial screw systems.

A total of 4 constructs were tested. These included: 1) an external fixation system; 2) a mono-axial pedicle screw system; 3) a polyaxial pedicle screw system (Click'X, a trademark of Synthes Inc., West Chester, Pa.); and 4) another polyaxial pedicle screw system (Pangea, a trademark of Synthes Inc., West Chester, Pa.). All constructs were assembled to have an active length of the longitudinal element equal to 280 mm. For the pedicle screws systems, screws were inserted into the test blocks, leaving an approximate 15 mm gap between screw head and test block. This resulted in a construct moment arm of 75 mm. The external fixator constructs were assembled with a 145 mm construct moment arm as this is where the fixator connection was measured to lie in a clinical setting.

Test Apparatus 1) an MTS RT/50 Electromechancial Test Frame, from MTS Corp. (Eden Praire, Minn.), Calibrated: 2/2008; and 2) an MTS Bionix Electromechanical Torsion Test Frame, from MTS Corp. (Eden Praire, Minn., Calibrated: 3/2008.

Test Procedure

All constructs were tested first in axial compression. Loads were applied in the elastic range (20 mm displacement). Once axial testing was completed, 3 components were tested in torsion, within the elastic range (10°), and 2 were to failure. The three components tested within the elastic range (axial and torsion) were then retested in axial compression until failure.

Axial Testing: Standard clevis fixtures were rigidly attached to the load cell and lower platen of the test machine. Constructs were mounted to the clevis fixtures using 12.7 mm diameter steel hinge pins.

An axial tensile load was applied to the construct at a test speed of 5 mm/min. Load-displacement curves were acquired for each construct tested and bending yield load, stiffness and ultimate bending failure load were calculated, as applicable. Yield load will calculation are based upon 0.020× the active length (5.6 mm). Note: testing was performed for a maximum of 75 mm of axial displacement. Results are shown in Table 1.

Torsion Testing: Clevis fixtures that prevented rotation of the test block were rigidly attached to the load cell and lower plate of the test machine. Constructs were mounted to the clevis fixtures using 12.7 mm diameter steel hinge pins. Spacers, that prevent test block rotations about the hinge pins, were manually set.

An angular displacement was applied to the construct at a test speed of 60°/min. Axial load was maintained at 0 Newton. Torque-angular displacement curves were acquired for each construct tested and torsional yield load, stiffness and ultimate torque will be calculated, as applicable. Yield torque was based upon a 5° offset. Note: testing was performed for a maximum of 60° or angular rotation. Results are shown in Table 2.

TABLE 1

Summary Results - Axial

| Type | Peak Load (N) | Yield Load (N) | Bending Stiffness (N/mm)* | p-value (vs. Ex Fix) |
|---|---|---|---|---|
| External Fixator | 160 ± 4 | 102 ± 3 | 2.88 ± 0.05 | — |
| USS Monoaxial | 370 ± 15 | *** | 4.01 ± 0.11 | >0.0001 |
| Click'X Polyaxial | 158 ± 1 | *** | 3.64 ± 0.11 | >0.0001 |
| Pangea Polyaxial | 137 ± 1 | *** | 3.63 ± 0.15 | >0.0001 |

TABLE 2

Summary Results - Torsional

| Type | Peak Torque (N-mm) | Yield Torque (N-mm) | Torsional Stiffness (N-mm/°)* | p-value (vs. Ex Fix) |
|---|---|---|---|---|
| External Fixator | 14.70 | 4.92 | 0.50 ± 0.07 | — |
| USS Monoaxial | 5.94 | 4.47 | 0.38 ± 0.01 | 0.0163 |
| Click'X Polyaxial | 6.93 | 4.40 | 0.38 ± 0.04 | 0.0124 |
| Pangea Polyaxial | 6.99 | 5.26 | 0.38 ± 0.01 | 00055 |

The results show that the construct of pedicle screws is superior to the external fixator in axial loading. However, the torsional stiffness is greater with the external fixator.

While this embodiment has been described with respect to pedicle screws 2 that have been attached to the anterior of each ilium and the bowed fixation rod 9 has been bowed anteriorly away from the pelvis, the invention can alternatively call for the attachment of the pedicle screws 2 to the posterior of the ilia and the bowed fixation rod 9 can be bowed posteriorly away from the pelvis.

Surgical Technique Second Embodiment

In an alternative embodiment, an anteriorly bowed subcutaneous elongated plate is used in place of the bowed rod. The elongated plate 10 is depicted in FIG. 8*a*. The plate 10 has at least one hole 11 in each end to accommodate the fixation means which affix the plate to the pelvis. Preferably the at least one hole 11 may be an elongated slot. More preferably the elongated slot is open on one end as shown in FIG. 8*a*. The elongated plate 10 may be bowed in a continuous arc or may have bends 13 (see FIG. 8*b*) to give the plate an approximation of an arc shape. The elongated plate 10 may be bent by the surgeon before insertion into the patient or may come pre-bent in a kit along with the fixation means. The pre-bent elongated plate 10 may come in a variety of lengths. It is believed that a most patients needs can be addressed using one size from a group of only three different sizes. The elongated plate 10 has a length much greater that its width and thickness. The elongated plate 10 may further include at least one additional hole 12 in each end through which stabilization fixation means may inserted into the pelvis.

Turning to FIG. 9, there is shown therein affixation devices useful for the present embodiment. Threaded rods 14 are used in conjunction with nuts 16 and 17 to hold the threaded rod 14 in the holes 11 at the ends of the elongated plate 10. Stabilization screws 15 are inserted through the additional holes 12 to further stabilize the elongated plate 10. The nuts 16 may be designed with a portion which fits into the hole/slot 11 assisting in fixing the threaded rod 14 to the elongated plate 10. The portion which fits into the hole/slot 11 may be threaded and may fit into threading in hole/slot 11. As with the previous embodiment, the elongated plate 10, threaded rods 14, stabilization screws 15, and nuts 16, 17 are all formed of a bio-compatible material such as, for example, titanium, stainless steel, or a bio-compatible and/or bio-adsorbable polymer.

FIGS. 10*a* to 10*l* depict the steps of a surgical method of using the elongated plate 10, threaded rods 14, stabilization screws 15, and nuts 16, 17 to fixate an unstable pelvic ring injury. The initial preparation is the same as that described above for the previous embodiment.

Figure 10A:
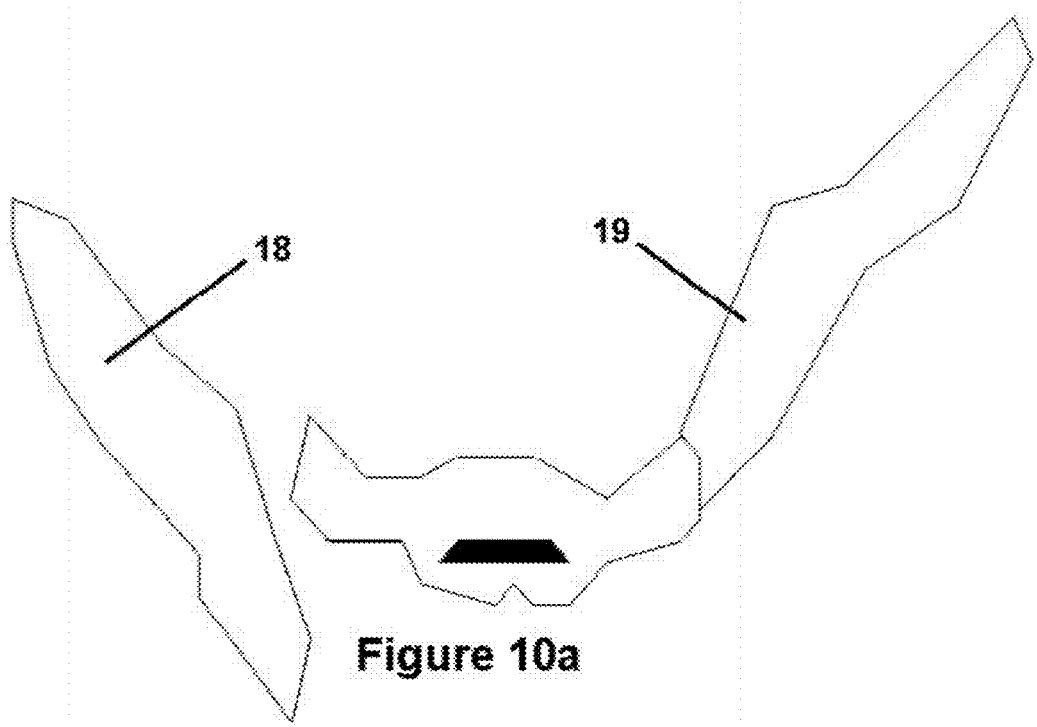
FIGS. 10a to 10l depict different stages in the surgical technique for fixation of the unstable pelvic ring injury using the elongated plate of FIGS. 8a and 8b using the threaded rods, screws, caps, and nuts of FIG. 9.
Figure 10B:
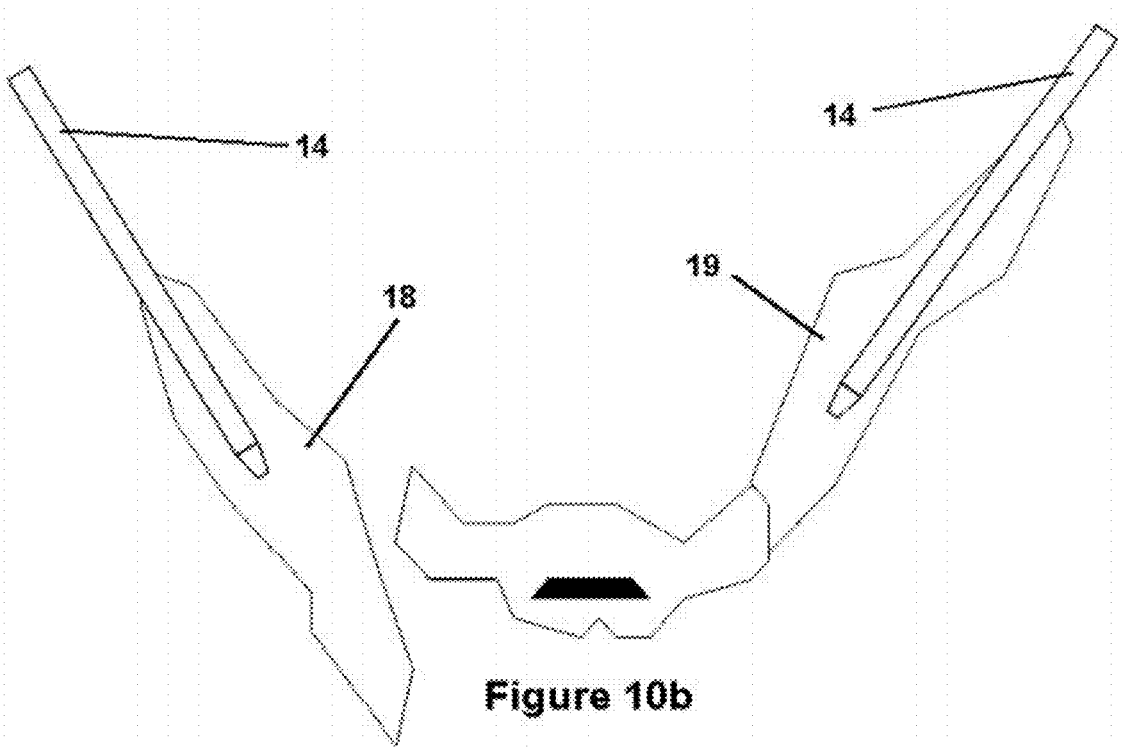

Referring now to FIG. 10*a* there is shown a schematic depiction of pelvis having an unstable pelvic ring injury. Specifically shown is an unstable ilium 18 and an intact ilium 19. It should be noted that the pelvic ring injury may result in both ilia being unstable and the inventive method for stabilization would be the same. Herein after the ilia will be known as the first and second ilium. Initially, threaded rods 14 are placed into both ilia 18, 19, as shown in FIG. 10*b*. Note that the threaded rod 14 which is affixed to the second ilium 18 is not fully inserted at this stage of the procedure.

Figure 10C:
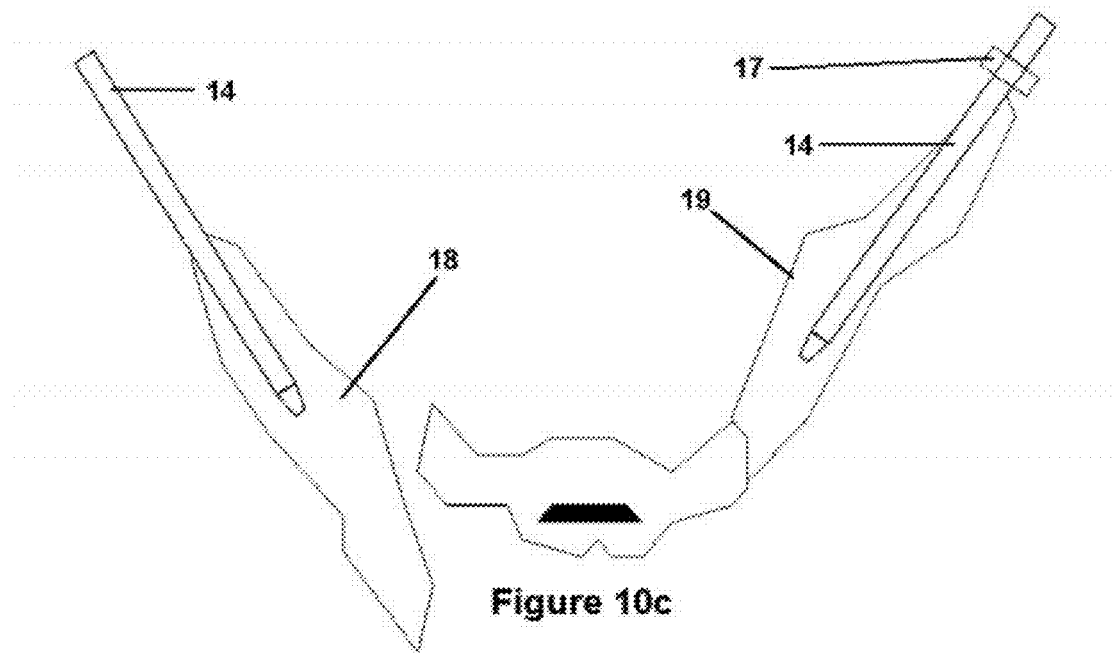
Figure 10D:
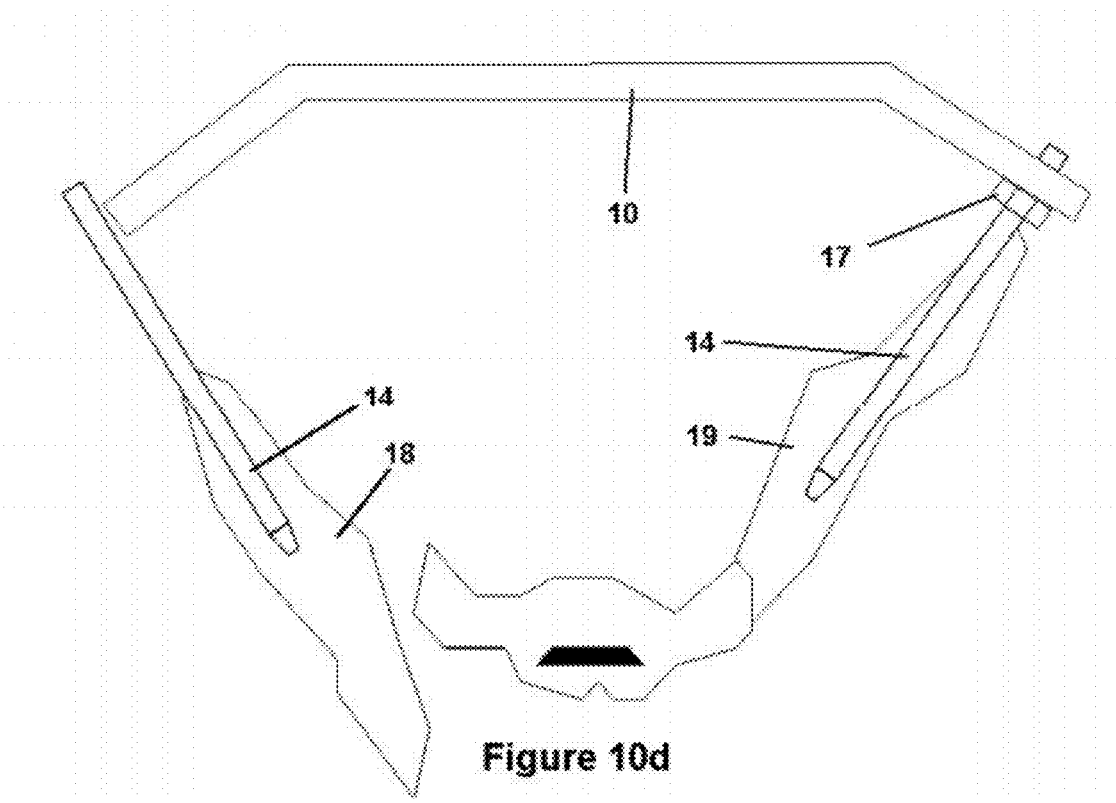

As in the previous embodiment, the threaded rods are placed into the supra-acetabular position using the technique described above. Once the threaded rods 14 are placed into both ilia 18, 19, a first threaded nut 17 is placed onto the threaded rod 14 which is affixed to the first ilium 19 as shown in FIG. 10*c*. One end of the elongated plate 10 is placed onto the threaded rod 14 which is affixed to the first ilium 19. The threaded rod 14 is inserted into the hole/slot 11 and the elongated plate rests adjacent the first threaded nut 17 as shown in FIG. 10*d*.

Figure 10E:
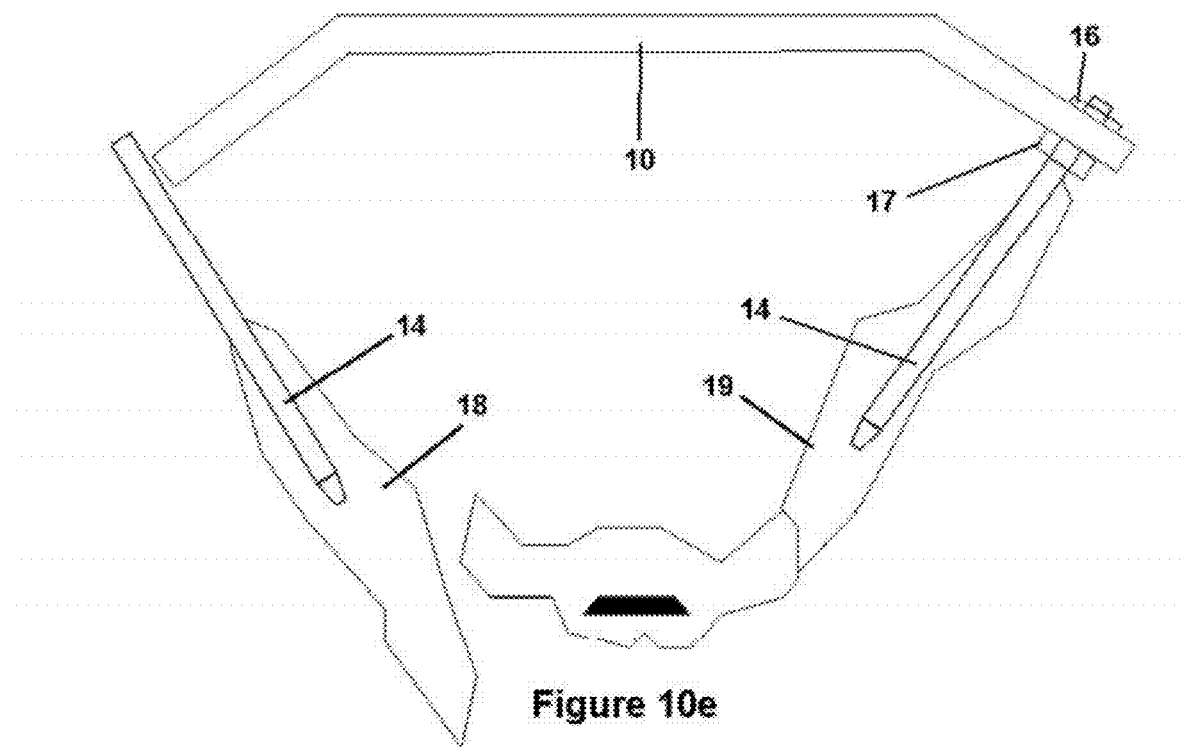
Figure 10F:
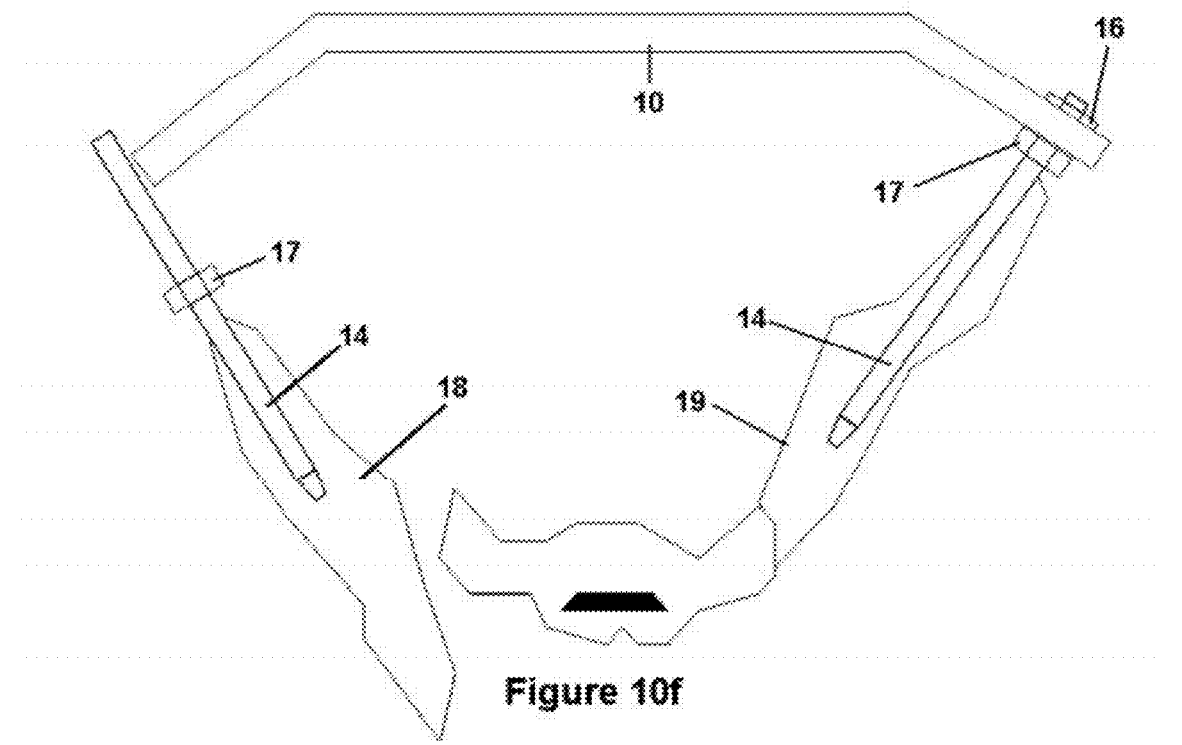
Figure 10G:
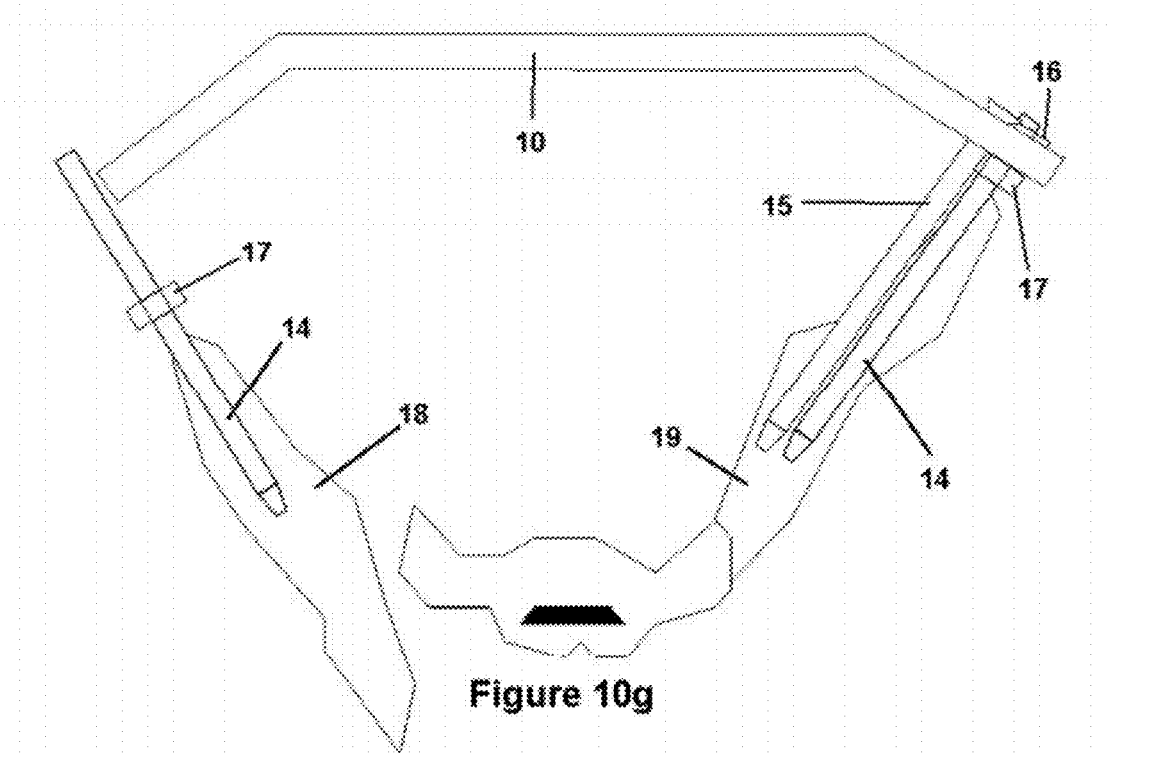

Once the plate is in place on the threaded rod 14 which is affixed to the first ilium 19, a second threaded nut 16 is attached to threaded rod 14 which is affixed to the first ilium 19 and is used in conjunction with first threaded nut 17 to fix the position of elongated plate 10 as shown in FIG. 10*e*. Next, a first threaded nut 17 is attached to the threaded rod 14 which is affixed to the second ilium 18 and a threaded stabilization screw 15 is inserted through additional hole 12 in the end of elongated plate 10 into the first ilium as shown in FIG. 10*g*.

Figure 10H:
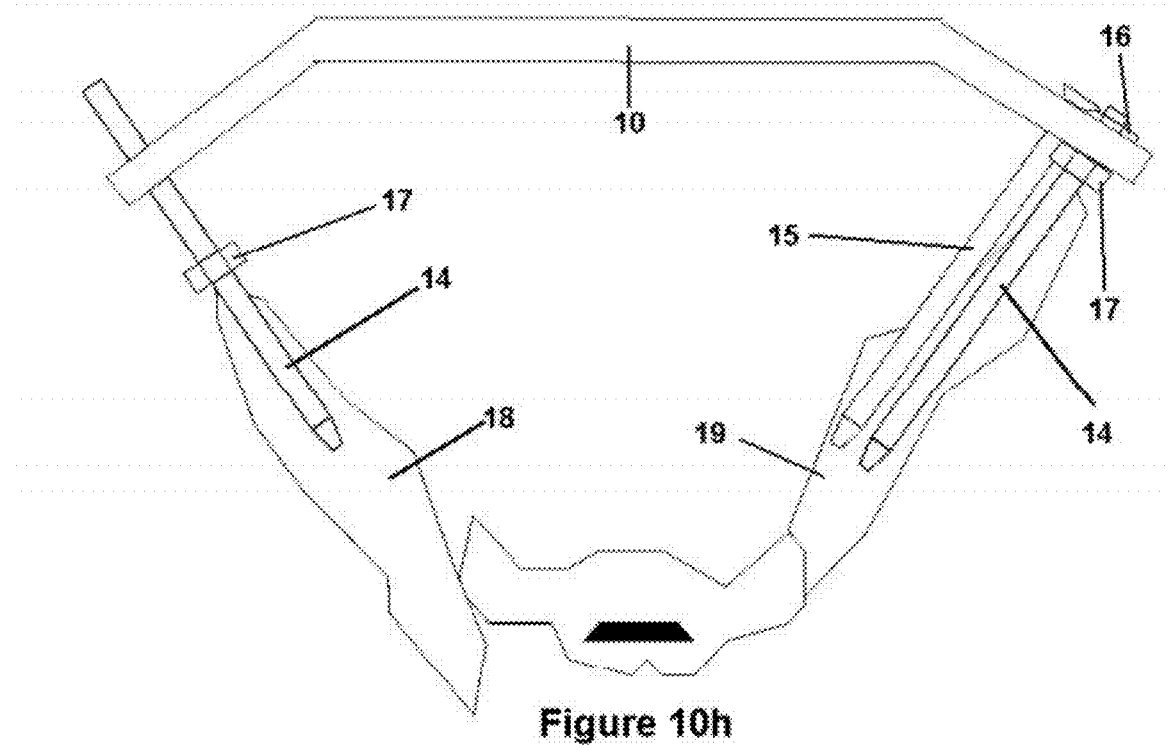
Figure 10I:
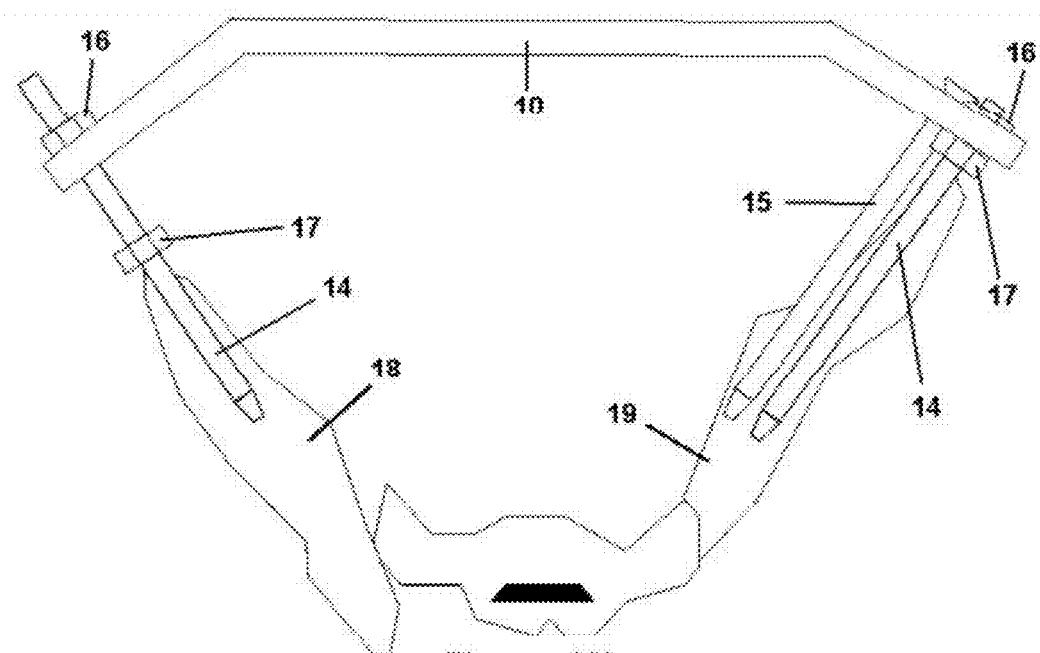
Figure 10J:
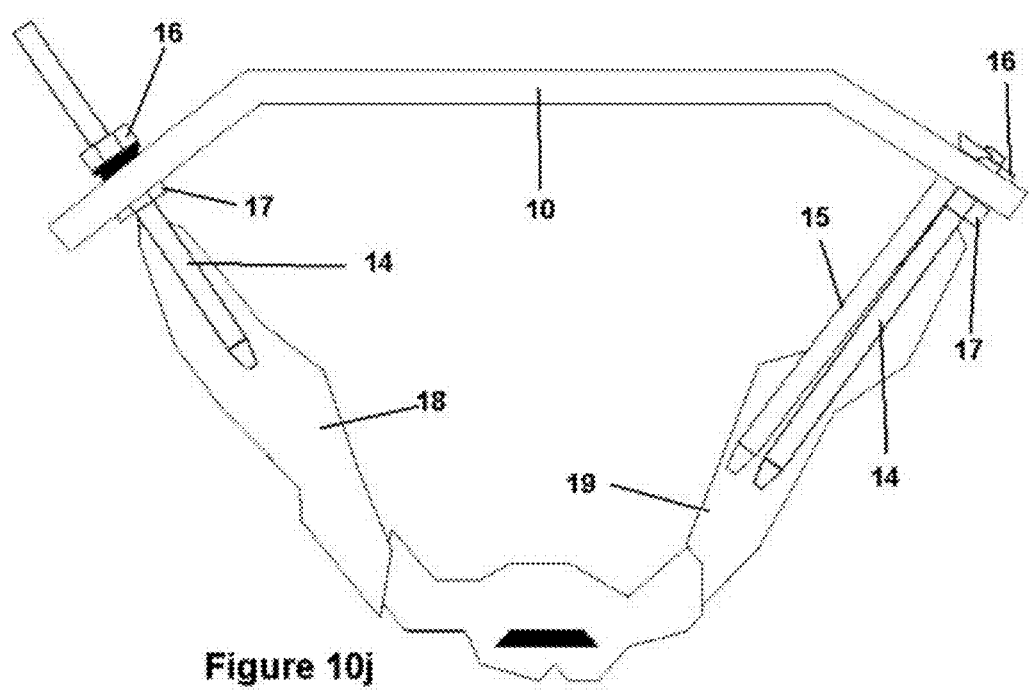

Next, the end of elongated plate 10 which is adjacent to the second ilium 18 is placed onto the threaded rod 14 which is affixed to the second ilium 18. This may be accomplished by slipping the threaded rod 14 into/through the open end of hole/slot 11 as shown in FIG. 10*h*. Next a second nut 16 is placed onto the threaded rod 14 which is affixed to the second ilium 18 a shown in FIG. 10*i*. Thereafter, second nut 16 which is threaded onto threaded rod 14 which is affixed to the second ilium 18 is tightened. As second nut 16 is tightened, the second ilium 18 is pulled into the proper position for fixation as shown in FIG. 10*j*.

Figure 10K:
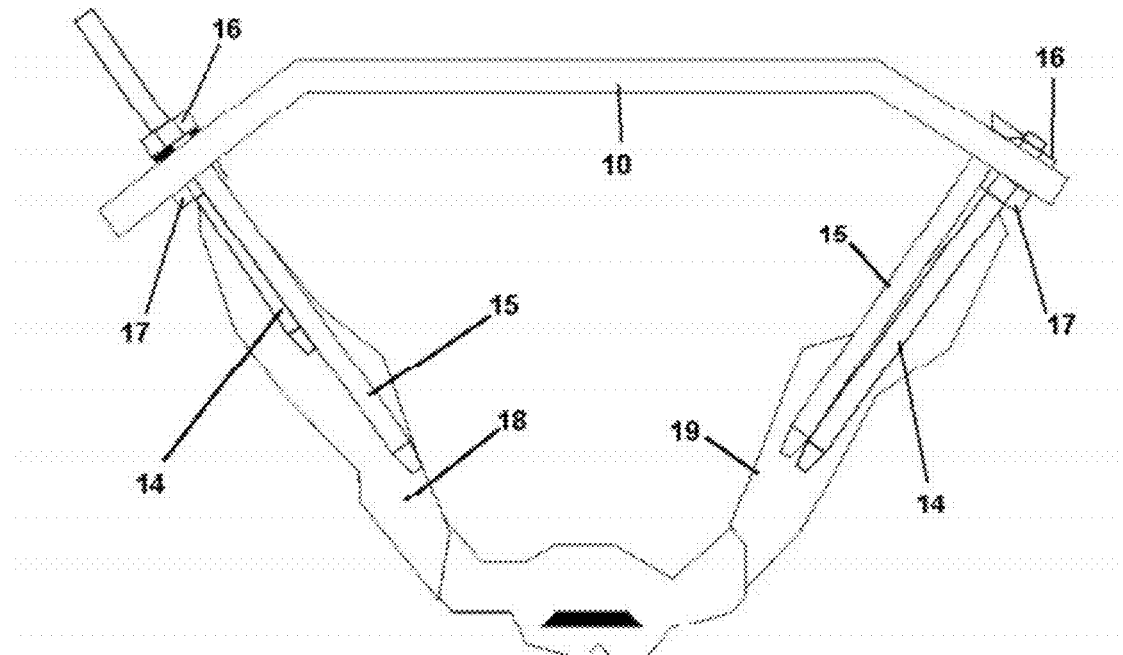
Figure 10L:
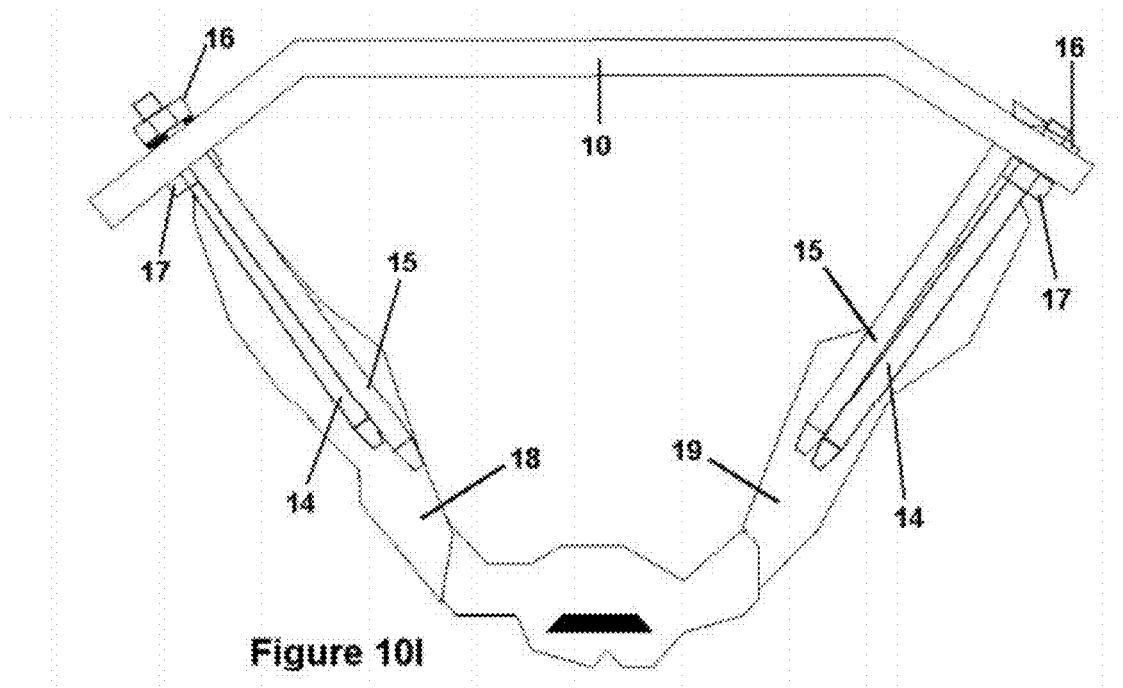

Once the second ilium is pulled into place and second nut 16 is fully tightened, another stabilization screw 15 is inserted into the second ilium 18 through the additional hole 12 in the end of the elongated plate 10 which is adjacent the second ilium 18 as shown in FIG. 10*k*. Finally, the threaded rod 14 which is affixed to the second ilium 18 is inserted the rest of the way into the second ilium 18 as shown in FIG. 10*l*.

This construct and procedure may be used alone (i.e. without posterior fixation) for transporting the trauma patient or with posterior fixation (using, for example, the iliosacral screw technique described above) for a definitive fixation solution.

Surgical Technique Third Embodiment

In yet another embodiment, an anteriorly bowed subcutaneous elongated plate is used in place of the bowed rod and a second plate is used on the posterior in place of the iliosacral screws. The two plates are shown in FIGS. 11a-11d. The side view and top view of the posterior plate 10" are depicted in FIGS. 11a and 11b. The posterior plate 10" has at least two holes 11 in each end thereof to accommodate the fixation means which affix the plate to the pelvis and the sacrum. The outermost holes 11 will be used to affix the posterior plate 10" to the ilia of the pelvis. The innermost holes 11 will be used to affix the posterior plate 10" to the sacrum. The posterior plate 10" has bends 13 to give the plate a shape that allows for fixation to the ilia of the pelvis and the sacrum, wile pressing against the posterior of the sacrum.

The side view and top view of the elongated anterior plate 10' are depicted in FIGS. 11c and 11d. The elongated anterior plate 10' has at a hole 11 in each end to accommodate the fixation means which affix the plate to the ilia of the pelvis. The elongated anterior plate 10' may be bowed in a continuous arc or may have bends 13 to give the plate an approximation of an arc shape. The elongated anterior plate 10' may be bent by the surgeon before insertion into the patient or may come pre-bent in a kit along with the fixation means. The pre-bent elongated anterior plate 10' may come in a variety of lengths. It is believed that a most patients needs can be addressed using one size from a group of only three different sizes. The elongated anterior plate 10' has a length much greater that its width and thickness.

Figure 12A:
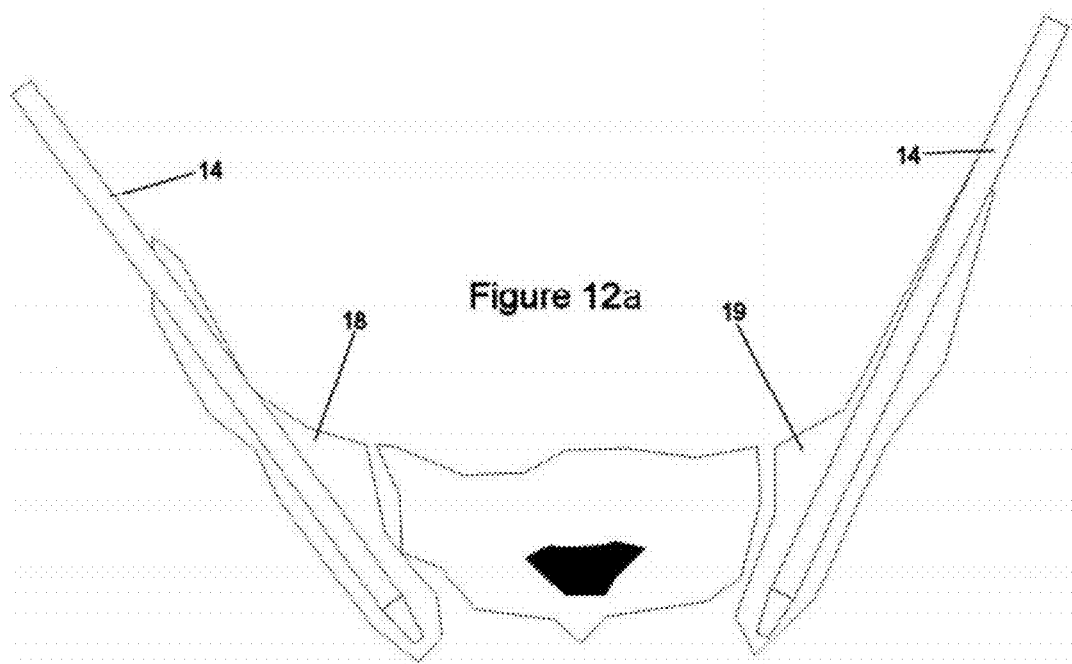

Turning to FIG. 12a, it can be seen that the affixation means for the present embodiment are the threaded rods 14 of FIG. 9 which are used in conjunction with nuts 16 and 17 to hold the threaded rod 14 in the holes 11 at the ends of the elongated plates 10' and 10". The threaded rods are inserted into the ilia 18 and 19 at the anterior superior iliac spine (ASIS) and are directed through the ilia toward the posterior superior iliac spine (PSIS). The rods do not protrude out of the PSIS region but rather remain within the ilia terminating near the surface of the PSIS.

Figure 12B:
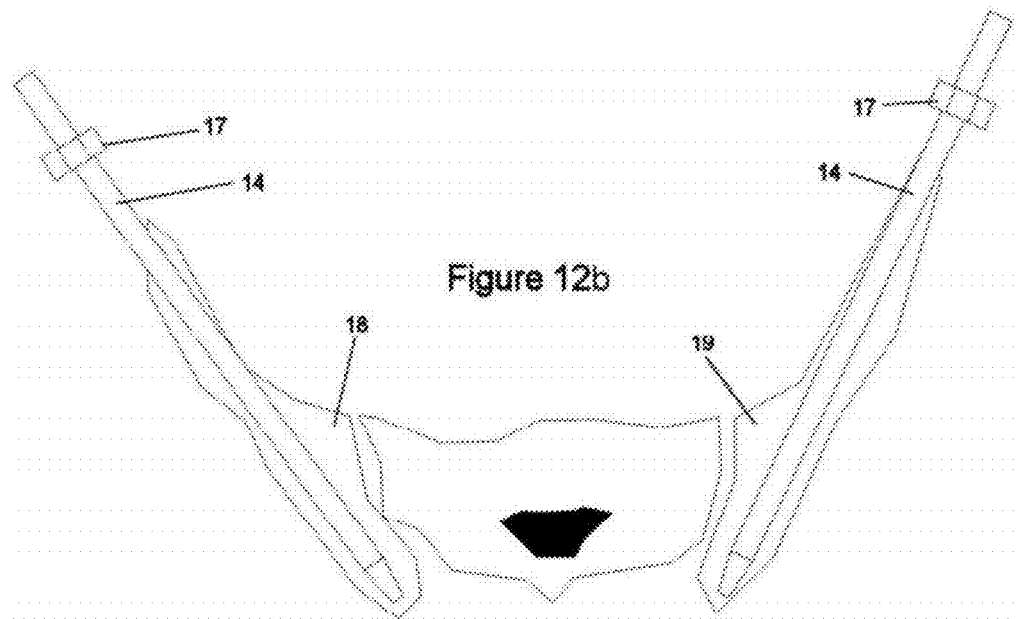
Figure 12C:
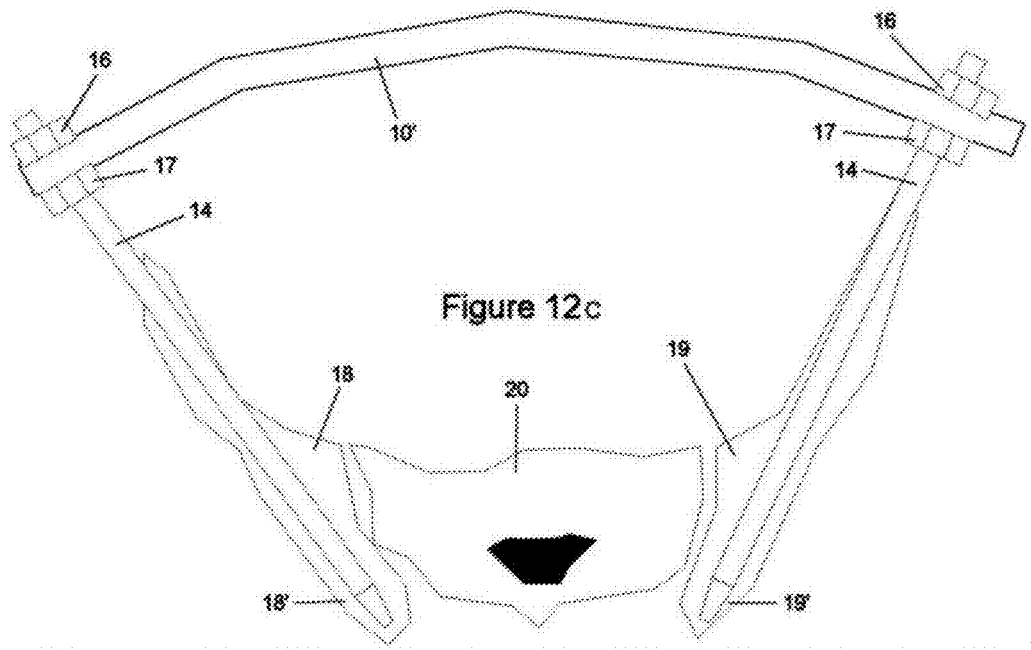

FIG. 12b shows how a nut 17 is attached to the anterior end of each threaded rod 14. The nut may be snugged to the ilia or remain remote from the ilia depending on the requirement of avoiding damage to muscles in the vicinity of the ASIS. Once the nuts 17 are in place, the anterior elongated plate 10' is inserted subcutaneously from one ilium to the other and the anterior plate 10' is affixed to the threaded rods 14 via the holes 11 in the anterior plate 10' as shown in FIG. 12c. Once the anterior plate 10' is in place, nuts 16 are threaded onto the threaded rods 14 and tightened to the anterior plate 10' to firmly affix the plate 10' to the rods 14.

Figure 12D:
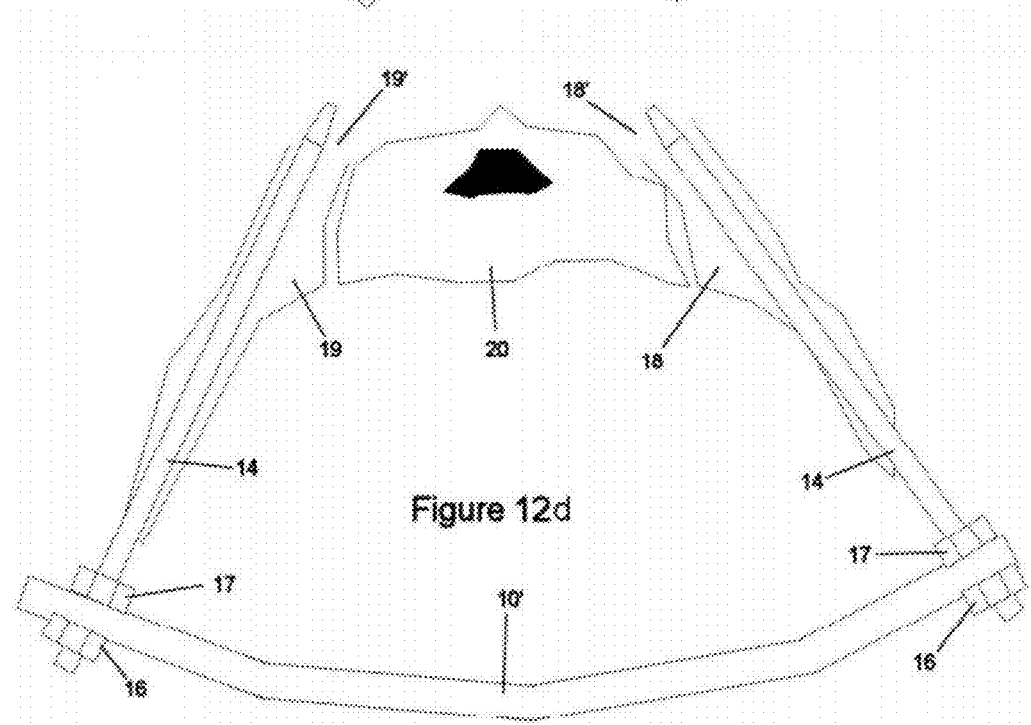
Figure 12E:
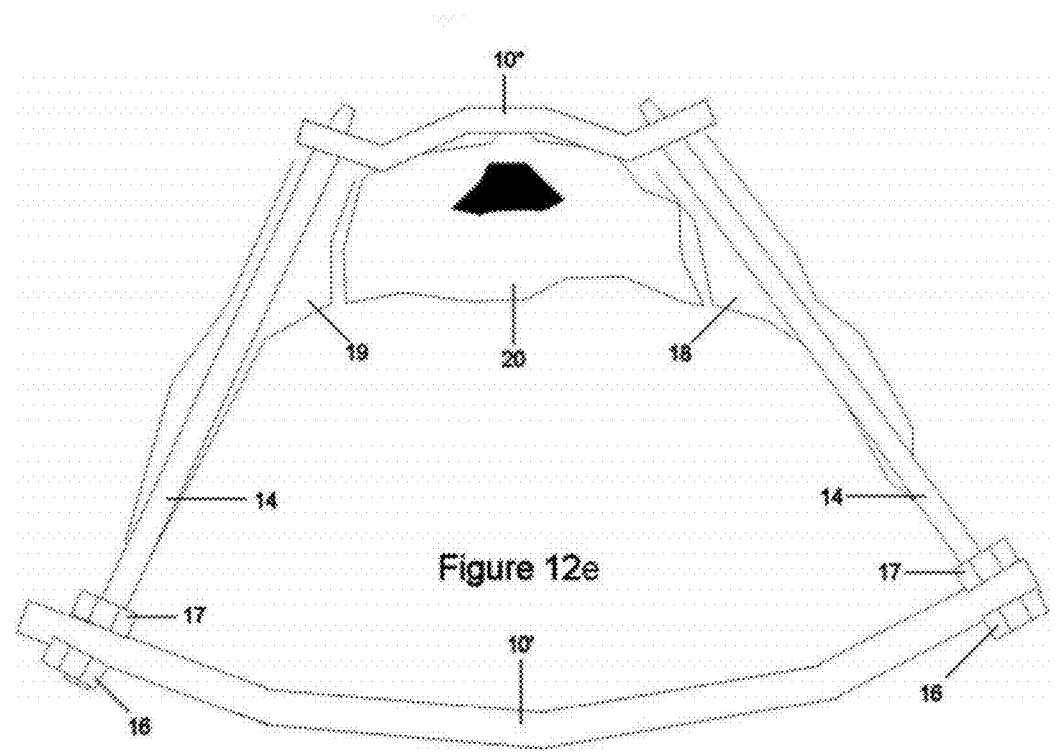
Figure 12F:
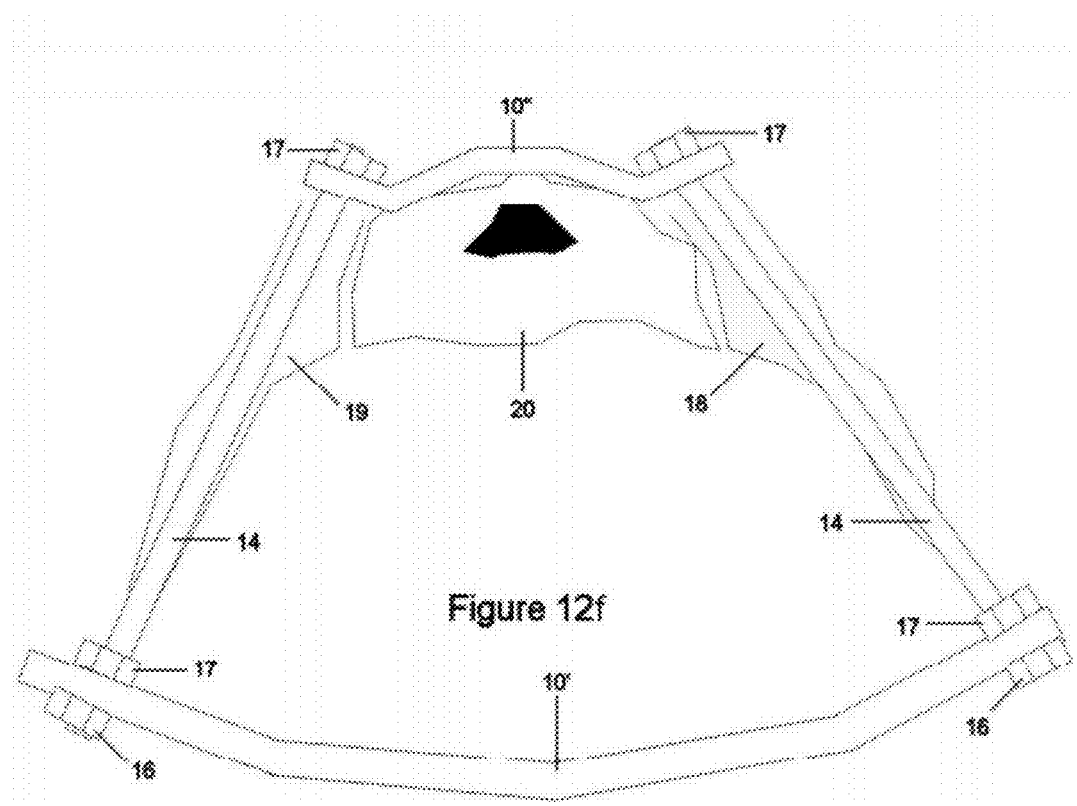

Next, the patient is flipped over and the posterior portion of the procedure is addressed. First the PSIS regions 18' and 19' of the ilia 18 and 19 are surgically removed to expose the posterior ends of the threaded rods 14 as shown in FIG. 12d. Once the PSIS regions 18' and 19' are removed, the posterior plate 10" is put into position with the outermost holes 11 affixed to the posterior end of the threaded rods 14 as shown in FIG. 12e. Then, nuts 17 are threaded onto the posterior ends of the threaded rods 14 and snugged tightly against the posterior plate 10", as shown in FIG. 12f. Finally bone screws 1 are inserted through the innermost holes 11 in the posterior plate 10" and into the sacrum 20 to finish stabilizing the posterior fixator.

It should be noted that in alternative embodiments, the anterior and/or posterior fixators may comprise a bowed rod rather than a plate. Of course this would require different means to attach the bowed rod to the threaded rod. Such different attachment means are known in the surgical arts.

It is to be further expected that considerable variations may be made in the embodiments disclosed herein without departing from the spirit and scope of this invention. Accordingly, the significant improvements offered by this invention are to be limited only by the scope of the following claims.

I claim:

1. A surgical method for minimally invasive treatment of unstable pelvic ring injuries comprising the steps of:
    affixing at least one fixation means to each of the first and second ilium of the pelvis; said fixation means comprising a threaded rod which is inserted into the ilium at the ASIS and extends through the ilium to the PSIS;
    attaching a rigid, anteriorly bowed subcutaneous elongated anterior plate to said at least one fixation means on each of said first and second ilium, anterior to the pelvis; and
    attaching a subcutaneous posterior plate to said at least one fixation means on each of said first and second ilium, posterior to the pelvis.

2. The surgical method of claim 1, wherein said step of affixing said threaded rod comprises the steps of:
    creating a longitudinal incision centered on the Anterior Superior Iliac Spine (ASIS);
    bluntly dissecting through the soft tissues;
    using fluoroscopic imaging to identify the starting point for the threaded rod;
    opening the cortex of the ilium at said starting point with a drill;
    establishing a corridor between the inner and outer cortices of the ilium using a pedicle finder; and
    screwing said threaded rod into said corridor.

3. The surgical method of claim 2, wherein said step of screwing said threaded rod into said corridor comprises screwing said threaded rods such that the threaded rods extend through the ilium to the PSIS.

4. The surgical method of claim 3, comprising the further step of subcutaneously tunneling said elongated anterior plate from one of said fixation means on one ilium to another of said fixation means on the other ilium, anterior to the pelvis, before said step of attaching said elongated anterior plate.

5. The surgical method of claim 4, wherein said elongated anterior plate has at least one hole in each end to accommodate said threaded rod fixation means which affix said plate to the anterior of each of said first and second ilium of the pelvis.

6. The surgical method of claim 5, wherein said step of attaching said elongated anterior plate further includes the steps of:
    threading a first threaded nut onto each of said threaded rods affixed to each of said first and second ilium of the pelvis;
    inserting one of said threaded rods affixed to said ilia into said holes in the either end of said elongated plate, said elongated plate resting on said first threaded nuts;
    threading a second threaded nut onto each of said threaded rods affixed to said ilia; and
    tightening said second threaded nuts against said elongated anterior plate such that said first threaded nuts and said second threaded nuts hold said elongated anterior plate securely to said threaded rod affixed to said ilia.

7. The surgical method of claim 1, wherein said elongated anterior plate has bends to give the plate an approximation of an arc shape.

8. The surgical method of claim 7, wherein said elongated anterior plate is positioned with the arc anterior to avoid any potential compressive complications to genitourinary or neurovascular structures prior to said step of attaching.

9. The surgical method of claim 1, wherein said subcutaneous posterior plate has a first hole in each end to accommodate said threaded rod fixation means which affix said subcutaneous posterior plate to the posterior of each of ilium of the pelvis.

10. The surgical method of claim 9, wherein said step of attaching a subcutaneous posterior plate to said threaded rods, further comprises the step of:
removing the ilium bone adjacent to the posterior end of said threaded rods, prior to attaching said subcutaneous posterior plate.

11. The surgical method of claim 10, wherein said step of attaching a subcutaneous posterior plate to said threaded rods, further comprises the step of:
subcutaneously tunneling said subcutaneous posterior plate from one of said fixation means on one ilium to another of said fixation means on the other ilium, posterior to the pelvis, before said step of attaching said subcutaneous posterior plate.

12. The surgical method of claim 11, wherein said step of attaching a subcutaneous posterior plate to said threaded rods, further comprises the step of:
inserting the posterior ends of said threaded rods into said holes in the either end of said subcutaneous posterior plate, said subcutaneous posterior plate resting on said ilia and the sacrum.

13. The surgical method of claim 12, wherein said step of attaching a subcutaneous posterior plate to said threaded rods, further comprises the steps of:
threading a threaded nut onto each of said posterior end of said threaded rods affixed to said ilia; and
tightening said threaded nuts against said subcutaneous posterior plate such that said threaded nuts hold said subcutaneous posterior plate securely to said threaded rod pressed against said ilia and said sacrum.

14. The surgical method of claim 13, wherein said subcutaneous posterior plate has a second hole in each end, interiorly position from said first hole to accommodate sacral fixation screws, and
said step of attaching a subcutaneous posterior plate to said threaded rods, further comprises the step of:
inserting sacral fixation bone screws through each of said second holes and into said sacrum.

15. The surgical method of claim 1 comprising the further step of leaving said fixation means and said plates attached to the pelvis for 8 to 12 weeks and thereafter removing said fixation means and said plates.

* * * * *